(12) United States Patent
Henry et al.

(10) Patent No.: US 11,073,451 B2
(45) Date of Patent: *Jul. 27, 2021

(54) BIOCOMPATIBLE METHOD OF FUNCTIONALISING SUBSTRATES WITH INERT SURFACES

(71) Applicant: KODE BIOTECH LIMITED, Auckland (NZ)

(72) Inventors: Stephen Micheal Henry, Auckland (NZ); Stephen Robert Parker, Auckland (NZ); Nicolai Vladimirovich Bovin, Moscow (RU); Igor Leonidovich Rodionov, Pushchino (RU)

(73) Assignee: KODE BIOTECH LIMITED, Auckland (NZ)

( * ) Notice: Subject to any disclaimer, the term of this patent is extended or adjusted under 35 U.S.C. 154(b) by 52 days.

This patent is subject to a terminal disclaimer.

(21) Appl. No.: 16/284,093

(22) Filed: Feb. 25, 2019

(65) Prior Publication Data

US 2019/0195759 A1 Jun. 27, 2019

Related U.S. Application Data

(63) Continuation-in-part of application No. 15/363,250, filed on Nov. 29, 2016, now Pat. No. 10,215,672, which is a continuation of application No. 14/366,889, filed as application No. PCT/NZ2012/000242 on Dec. 19, 2012, now Pat. No. 9,528,139, application No. 16/284,093, which is a continuation-in-part of application No. 15/585,296, filed on May 3, 2017, now abandoned, which is a continuation-in-part of application No. PCT/IB2016/052735, filed on May 12, 2016.

(30) Foreign Application Priority Data

| Dec. 19, 2011 | (NZ) | ......................................... 597207 |
| Aug. 9, 2012 | (NZ) | ......................................... 601745 |
| Nov. 3, 2014 | (AU) | .............................. 2014904423 |
| May 20, 2015 | (AU) | .............................. 2015901844 |
| Nov. 3, 2015 | (WO) | ............... PCT/NZ2015/050181 |

(51) Int. Cl.

| G01N 1/40 | (2006.01) |
| C08G 64/42 | (2006.01) |
| G01N 33/543 | (2006.01) |
| C12Q 1/02 | (2006.01) |
| C12Q 1/24 | (2006.01) |
| B01D 65/08 | (2006.01) |
| B01L 3/00 | (2006.01) |
| B01D 69/14 | (2006.01) |
| B01D 67/00 | (2006.01) |
| B01D 63/08 | (2006.01) |

(52) U.S. Cl.
CPC ........... *G01N 1/4077* (2013.01); *B01D 65/08* (2013.01); *C08G 64/42* (2013.01); *C12Q 1/02* (2013.01); *C12Q 1/24* (2013.01); *G01N 33/54353* (2013.01); *G01N 33/54393* (2013.01); *B01D 63/087* (2013.01); *B01D 67/0088* (2013.01); *B01D 69/144* (2013.01); *B01L 3/5635* (2013.01); *B01L 2300/0681* (2013.01); *B01L 2300/12* (2013.01); *G01N 2001/4088* (2013.01)

(58) Field of Classification Search
CPC .............................................. G01N 2001/4088
See application file for complete search history.

(56) References Cited

U.S. PATENT DOCUMENTS

| 3,492,135 | A | 1/1970 | Clauss |
| 3,567,420 | A | 3/1971 | Legator et al. |
| 5,171,678 | A | 12/1992 | Behr et al. |
| 5,624,958 | A | 4/1997 | Isaacs et al. |
| 8,236,337 | B2 | 8/2012 | Reid et al. |
| 2002/0022264 | A1 | 2/2002 | Sullivan et al. |
| 2007/0224275 | A1 | 9/2007 | Reid et al. |
| 2010/0028823 | A1 | 2/2010 | Reid et al. |
| 2010/0158966 | A1 | 6/2010 | Reid et al. |
| 2010/0158967 | A1 | 6/2010 | Reid et al. |
| 2011/0042299 | A1 | 2/2011 | Zhang et al. |
| 2012/0021430 | A1 | 1/2012 | Bovin et al. |

(Continued)

FOREIGN PATENT DOCUMENTS

| EP | 0 394 111 | 10/1990 |
| JP | 2-62806 | 3/1990 |

(Continued)

OTHER PUBLICATIONS

Behr et al (1989) *Efficient gene transfer into mammalian primary endocrine cells with lipopolyamine-coated DNA* Proc. Natl. Acad. Sci. USA, 86, 6982-6986.

Blagbrough et al (1997) *Polyamines and polyamine amides as potent selective receptor probes, novel therapeutic lead compounds and synthetic vectors in gene therapy* Pharmaceutical Sciences, 3, 223-233.

(Continued)

*Primary Examiner* — Bin Shen

(74) *Attorney, Agent, or Firm* — Nixon & Vanderhye P.C.

(57) ABSTRACT

Methods of treating an inert surface of a substrate to improve the adherence to the treated surface of micro-dimensioned particles including the steps of: contacting the inert surface with in an aqueous dispersion of a construct of the structure F-S-L; and then washing the surface with an aqueous vehicle to provide the treated surface, where F is a polyamine; S is —CO(CH$_2$)$_2$CO—, —CO(CH$_2$)$_3$CO—, —CO(CH$_2$)$_4$CO— or —CO(CH$_2$)$_5$CO—; and L is a diacyl- or dialkyl-glycero-phospholipid.

7 Claims, 19 Drawing Sheets

(56) References Cited

U.S. PATENT DOCUMENTS

| | | | |
|---|---|---|---|
| 2012/0288813 A1 | 11/2012 | Reid et al. | |
| 2013/0165595 A1 | 6/2013 | Reid et al. | |

FOREIGN PATENT DOCUMENTS

| | | |
|---|---|---|
| JP | 2001-040273 | 2/2001 |
| JP | 2015-020951 | 2/2015 |
| WO | WO 00/62813 | 10/2000 |
| WO | WO 2007/008293 | 1/2007 |
| WO | WO 2008/133534 | 11/2008 |
| WO | WO 2009/048343 | 4/2009 |
| WO | WO 2009/056955 | 5/2009 |
| WO | WO 2009/087373 | 7/2009 |
| WO | WO 2010/080086 | 7/2010 |
| WO | WO 2011/002310 | 1/2011 |
| WO | WO 2012/099477 | 7/2012 |
| WO | WO 2012/121610 | 9/2012 |
| WO | WO 2013/081471 | 6/2013 |
| WO | WO 2014/007649 | 1/2014 |
| WO | WO 2014/070687 | 5/2014 |

OTHER PUBLICATIONS

Blake, D.A., et al; "FSL Constructs: A Simple Method for Modifying Cell/Virion Surfaces with a Range of Biological Markers Without Affecting their Viability"; *Journal of Visualized Experiments;* Issue 54, e3289, pp. 1-9 (2011).

Byk et al (1998) *Synthesis, activity, and structure-activity relationship studies of novel cationic lipids for DNA transfer* J. Med. Chem. 1998, 41, 224-235.

Carmona-Ribeiro, A.M.; "Interactions between Cationic Liposomes and Drugs or Biomolecules"; *An Acad. Bras. Ci.,* vol. 72 (1), pp. 39-43 (2000).

Chemburu, S., et al; "Conjugated Polyelectrolyte Supported Bead Based Assays for Phospholipase $A_2$ Activity"; *J. Phys. Chem. B;* vol. 112, pp. 14492-14499 (2008).

Cheng, C.J., et al; "Enhanced siRNA delivery into cells by exploiting the synergy between targeting ligands and cell-penetrating peptides"; *Biomaterials;* vol. 32, pp. 6194-6203 (2011).

Dekkers et al, J. of Applied Polymer Science, 30:2389-2400, 1985.

Distler (1967) *The chemistry of Bunte salts* Angew. Chem. Internat. Edit. vol. 6, No. 6, 544.

Felgner et al (1994) *Enhanced gene delivery and mechanism studies with a novel series of cationic lipid formulations* The Journal of Biological Chemistry, 269, 4, 2550-2561.

Gallo et al (2014) *Antibacterial Surface Treatment for Orthopaedic Implants* Int. J. Mol. Sci. 2014, 15, 13849-13880.

Geall and Blagbrough (2000) *Homologation of polyamines in the rapid synthesis of lipospermine conjugates and related lipoplexes* Tetrahedron 56, 2249-2460.

Goodwin, A.P., et al; "Phospholipid-Dextran with a Single Coupling Point: A Useful Amphiphile for Functionalization of Nanomaterials"; *JACS Articles;* Published on Web Dec. 5, 2008, vol. 131, pp. 289-296 (2009), (XP007915884).

Heathcote, D., et al; "Novel antibody screening cells, MUT+ Mur Kodecytes, created by attaching peptides onto red blood cells"; *Transfusion,* vol. 50, Issue 3, pp. 635-641 (2010).

Jeney and Zsolnai (1959) *Bacteriostatic action of organic selenocyanates* Naturwissenschaften, 46, 231 [CAPLUS database abstract].

Kato et al (2003) *Immobilized culture of nonadherent cells on an oleyl poly(ethylene glycol) ether-modified surface* BioTechniques 35, 1014-1021.

Kerstetter and Gramlich (2014) *Nanometer-scale self-assembly of amphiphilic copolymers to control and prevent biofouling* J. Mater. Chem. B, 2014, 2, 8043-5052.

Kikuchi et al (1997) *Antimicrobial activities of squalamine mimics* Antimicrobial Agents and Chemotherapy, 41, 7, 1433-1438.

Kruszewski et al (2013) *Reducing Staphylococcus aureus biofilm formation on stainless steel 316L using functionalized self-assembled monolayers* NIH Public Access Author Manuscript Mater Sci Eng C Mater Biol Appl 33(4): 2059-2069.

Mamizuka and Carmona-Ribeiro (2007) *Cationic liposomes as antimicrobial agents* Communicating Current Research and Educational Topics and Trends in Applied Microbiology A. Méndez-Vilas (Ed.), 636.

Munro, J.C., et al; "Adsorption of Lipid-Functionalized Poly(ethylene glycol) to Gold Surfaces as a Cushion for Polymer-Supported Lipid Bilayers"; *Langmuir,* vol. 20, pp. 3339-3349 (2004).

Niyomtham et al (2015) *Synthesis and in vitro transfection efficiency of spermine-based cationic lipids with different central core structures and lipophilic tails* Bioorganic & Medical Chemistry Letters, 25, 496-503.

Numao et al (1981) *Showdomycin analogues: Synthesis and antitumor evaluation* J. Med. Chem. 1981, 24, 515-520.

Randazzo et al (2009) *A series of cationic sterol lipids with gene transfer and bactericidal activity* Bioorganic & Medicinal Chemistry 17, 3257-3265.

Remy et al (1994) *Gene transfer with a series of lipophilic DNA-binding molecules* Bioconjugate Chem. 5, 647-654.

Shi et al (2012) *Antibacterial and osteoinductive capability on orthopedic materials via cation-π interaction mediated positive charge* Journal of Materials Chemistry B, 2014, 00, 1-5.

Xie, M., et al; "PEG-interspersed nitrilotriacetic acid-functionalized quantum dots for site-specific labeling of prion proteins expressed on cell surfaces"; *Biomaterials;* vol. 31, pp. 8362-8370 (2010).

Zsolnai (1962) *Discovery of new fungicides. IV. Organic sulfur compounds* Biochemical Pharmacology, 11, 271-297 [CAPLUS database abstract].

International Preliminary Report on Patentability issued in PCT/IB2016/052735 dated Nov. 21, 2017.

International Preliminary Report on Patentability issued in PCT/NZ2015/050181 dated Feb. 22, 2017.

International Search Report issued in PCT/NZ2012/000242 dated Apr. 17, 2013.

International Search Report issued in PCT/IB2016/052735 dated Apr. 15, 2016.

A

B

A

B

BIOCOMPATIBLE METHOD OF FUNCTIONALISING SUBSTRATES WITH INERT SURFACES

This application is a continuation-in-part of U.S. application Ser. No. 15/363,250 filed Nov. 29, 2016, which is a continuation of U.S. application Ser. No. 14/366,889 filed Jun. 19, 2014 (now U.S. Pat. No. 9,528,139), which is a National Phase of PCT/NZ2012/000242 filed Dec. 19, 2012, which claims priority to New Zealand Application Nos. 601745 filed Sep. 8, 2012 and 597207 filed Dec. 19, 2011; and this application is a continuation-in-part of U.S. application Ser. No. 15/585,296 filed May 3, 2017, which is a continuation-in-part of PCT/IB2016/052735 filed May 12, 2016, which claims priority to PCT/NZ2015/050181 filed Nov. 3, 2015, and Australian Application Nos. 2015901844 filed May 20, 2015 and 2014904423 filed Nov. 3, 2014; and U.S. application Ser. No. 15/585,296 is also a CIP of PCT/NZ2015/050181, which also claims priority to Australian Application No. 2015901844, the contents of each of which are hereby incorporated by reference.

FIELD OF INVENTION

The invention relates to a biocompatible method of functionalising inert surfaces for use in biological applications. In particular, the invention relates to a biocompatible method of functionalising the inert surface of porous membranes and microspheres or nanospheres.

BACKGROUND ART

Filter membranes are routinely used in the analysis and preparation of biological samples. The surface of the substrate used in the manufacture of such membranes is purposefully selected to be antifouling, i.e. resistant to non-specific binding of components of the biological sample, and chemically inert.

Microbeads and microspheres are used for the isolation and separation of biomolecules from complex mixtures. Reactive molecules are adsorbed or coupled to the surface of the beads or spheres. When the beads or spheres are superparamagnetic biomagnetic separation techniques may be employed.

Membranes and microbeads or microspheres can be manufactured from various natural and synthetic materials including glass, metal, e.g. gold, and polymers, e.g. polycarbonate, polyethylene and polystyrene. Polystyrene is commonly used in biological applications as proteins readily adsorb onto its surface. Glass has limited use because of the limited ability to functionalise its surface.

The publication of Kato et al (2003) discloses a method of adhering otherwise non-adherent cells to surfaces using a biocompatible anchor.

It is an object of the present invention to provide a biocompatible method of localising functional moieties to the inert surface of a substrate. It is an object of the present invention to provide a method of treating a surface that is effective to promote the adherence of micro-dimensioned particles to the surface. These objects are to be read in the alternative with the object at least to provide the public with a useful choice.

STATEMENT OF INVENTION

In a first aspect the invention provides a method of functionalising an inert surface of a substrate comprising the step of contacting the surface of the substrate with an aqueous dispersion of a construct of the structure F-S-L, where F is a functional moiety, S is a spacer selected to provide a construct that is dispersible in water, and L is a diacyl- or dialkyl-glycerophospholipid.

Preferably, the method comprises the steps of:
1. contacting the surface of the substrate with an aqueous dispersion of a construct of the structure F-S-L; and then
2. washing the surface of the substrate with an aqueous vehicle to provide the functionalised surface.

Preferably, the inert surface consists of a substance selected from the group consisting of: glass, silver, polyamide, polycarbonate, polypropylene, polyethersulfone, polytetrafluoroethylene and polyvinylidene fluoride. More preferably, the inert surface is other than polystyrene. Preferably, the substrate is a fibre, membrane or microsphere.

Preferably, the contacting the surface of the substrate is by immersing the substrate in the aqueous dispersion of the construct. Most preferably, the contacting the surface of the substrate by immersing the substrate in the aqueous dispersion of the construct is when the substrate comprises fibres or microspheres.

Preferably, the contacting the surface of the substrate is by flooding the surface of the substrate with the aqueous dispersion of the construct. Most preferably, the contacting the surface of the substrate is by flooding the surface of the substrate with the aqueous dispersion of the construct when the substrate is a membrane comprising fibres.

In a first embodiment of the first aspect of the invention the substrate is a membrane comprised of cross-linked, fused or woven fibres. More preferably, the membrane is a filtration membrane. In a second embodiment of the first aspect of the invention the substrate is a microsphere. More preferably, the microsphere is a polycarbonate microsphere. In a third embodiment of the first aspect of the invention the substrate is a membrane comprising fibres.

Preferably, the construct is a water dispersible construct of the structure:

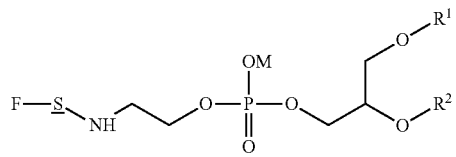

where F is a functional moiety, M is a monovalent cation, $R^1$ and $R^2$ are independently a $C_{14-20}$ acyl, alkyl or alkenyl group, preferably a $C_{16-18}$ acyl, alkyl or alkenyl group, and S is a spacer selected to provide a construct that is dispersible in water. More preferably, the construct is a water dispersible construct of the structure:

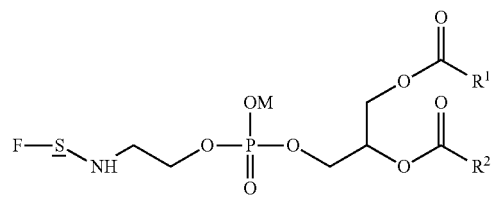

where $R^1$ and $R^2$ are independently a $C_{13-19}$ alkyl or alkenyl group, preferably a $C_{15-17}$ alkyl or alkenyl group. Yet more preferably, F—S— is of the structure $F\text{-}S_1\text{-}S_2\text{-}S_3\text{-}$ where:

$S_1$ is 2-aminoethyl, 3-aminopropyl, 4-aminobutyl, or 5-aminopentyl, $S_2$ is absent or

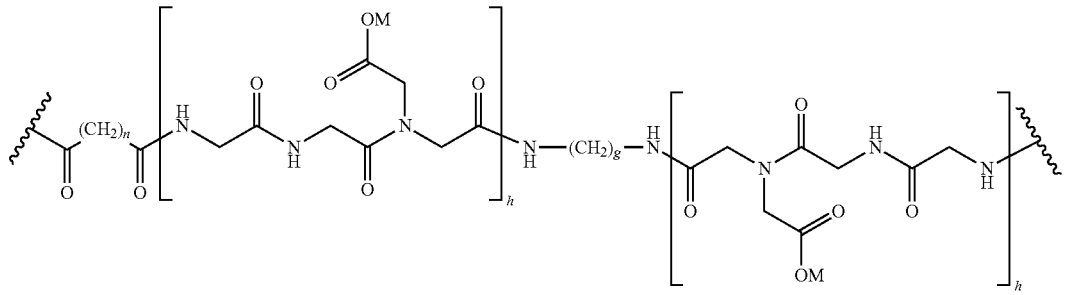

where g is the integer 1, 2 or 3, h is the integer 1, 2, 3 or 4, n is the integer 2, 3, 4 or 5, and $S_3$ is —CO(CH$_2$)$_2$CO—, —CO(CH$_2$)$_3$CO—, —CO(CH$_2$)$_4$CO— or —CO(CH$_2$)$_5$CO— when F is a mono-, di-, tri- or oligosaccharide;

$S_1$ is

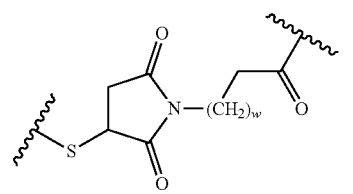

where w is the integer 1 or 2, $S_2$ is

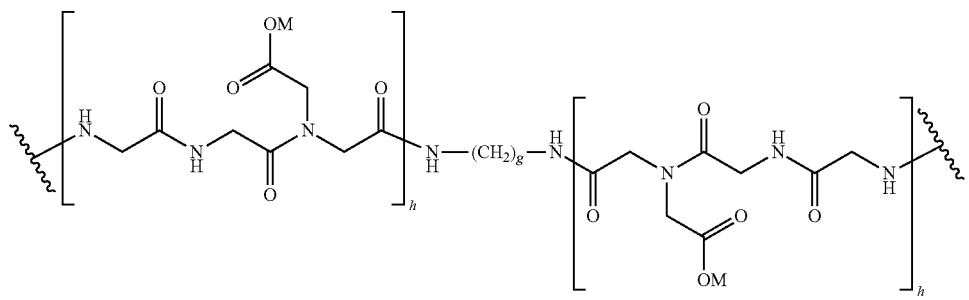

where g is the integer 1, 2 or 3 and h is the integer 1, 2, 3 or 4, and $S_3$ is —CO(CH$_2$)$_2$CO—, —CO(CH$_2$)$_3$CO—, —CO(CH$_2$)$_4$CO— or —CO(CH$_2$)$_5$CO— when F is a thioether conjugated oligopeptide;

$S_1$ is

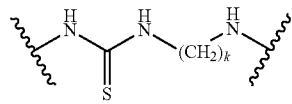

where k is the integer 4, 5 or 6, $S_2$ is absent and $S_3$ is —CO(CH$_2$)$_2$CO—, —CO(CH$_2$)$_3$CO—, —CO(CH$_2$)$_4$CO— or —CO(CH$_2$)$_5$CO— when F is a fluorophore of fluorescein or a derivative thereof;

$S_1$ is

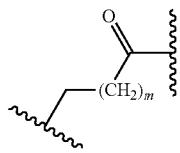

where m is the integer 1 or 2, $S_2$ is

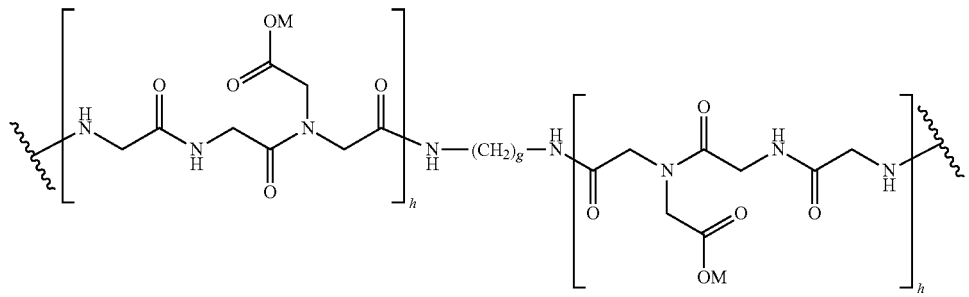

where g is the integer 1, 2 or 3 and h is the integer 1, 2, 3 or 4, and $S_3$ is —CO(CH$_2$)$_2$CO—, —CO(CH$_2$)$_3$CO—, —CO(CH$_2$)$_4$CO— or —CO(CH$_2$)$_5$CO— when F is biotin; or $S_1$ and $S_2$ are absent and $S_3$ is —CO(CH$_2$)$_2$CO—, —CO(CH$_2$)$_3$CO—, —CO(CH$_2$)$_4$CO— or —CO(CH$_2$)$_5$CO— when F is a polycation. Preferably, F is a polyamine. More preferably, F is of the structure:

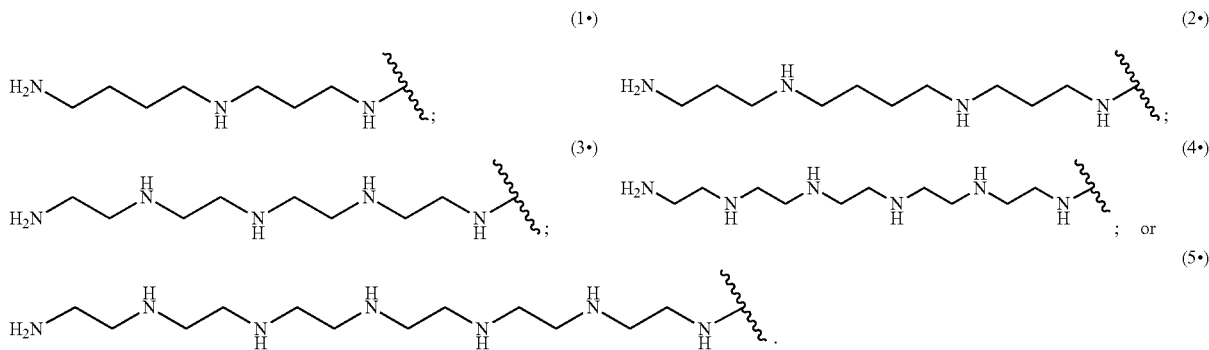

Most preferably, the construct is a water dispersible construct of the structure F-S-L as described in one or more of the specifications accompanying international application nos. PCT/NZ2005/000052 (publ. no. WO 2005/090368), PCT/NZ2006/000245 (publ. no. WO 2007/035116), PCT/NZ2008/000239 (publ. no. WO 2009/035347), PCT/NZ2008/000266 (publ. no. WO 2009/048343), PCT/NZ2010/000111 (publ. no. WO 2010/143983), PCT/NZ2012/000012 (publ. no. WO 2012/121610), PCT/NZ2012/000029 (publ. no. WO 2012/118388), PCT/NZ2012/000156 (publ. no. WO 2013/081471), PCT/NZ2015/050181 (publ. no. WO 2016/072863) and PCT/IB2016/052735 (publ. no. WO 2016/185331).

Typically, L is 1,2-O-dioleoyl-sn-glycero-3-phosphatidylethanolamine (DOPE) and 1,2-O-distearyl-sn-glycero-3-phosphatidylethanolamine (DSPE), most often 1,2-O-dioleoyl-sn-glycero-3-phosphatidylethanolamine (DOPE).

In a second aspect the invention provides a substrate comprising a construct of the structure F-S-L localised to its surface where the surface is inert, F is a functional moiety, S is a spacer selected to provide a construct that is dispersible in water, and L is a diacyl- or dialkyl-glycerophospholipid. Preferably, the inert surface is polycarbonate.

In a first embodiment of the second aspect the substrate is fibre. In a second embodiment of the second aspect the substrate is membrane.

In a third embodiment of the second aspect the substrate is a microsphere.

In a third aspect the invention provides a filter assembly comprising a membrane functionalised according to the method of the first aspect of the invention. Preferably, the filter assembly comprises a membrane functionalised according to the method of the first aspect of the invention and sealed between an inlet housing and an outlet housing.

In the description and claims of this specification the following acronyms, terms and phrases have the meaning provided.

"Alicyclic" means cyclic aliphatic. "Aliphatic" means alkanes, alkenes or alkynes or their derivatives and is used as a descriptor for compounds that do not have the special stability of aromatics.

"Alkanes" means a saturated hydrocarbon of the general formula $C_nH_{2n+2}$. "Alkenes" means unsaturated hydrocarbons that contain one or more double carbon-carbon bonds. "Alkynes" means unsaturated hydrocarbons that contain one or more triple carbon-carbon bonds. "Aromatic" means containing a benzene ring or having similar chemical properties. "Biocompatible" means not harmful or toxic to living tissue. "Boc" means tert-butoxycarbonyl. "Boc$_3$Spm" means ($N^1,N^4,N^9$-tri-tert-butoxycarbonyl)-1,12-diamino-4,9-diazadodecane. "Comprising" means "including", "containing" or "characterized by" and does not exclude any additional element, ingredient or step. "Consisting of" means excluding any element, ingredient or step not specified except for impurities and other incidentals. "Dispersible in water" means dispersible in pure, deionised water at 25° C. in the absence of organic solvents or surfactants to provide a dispersion at a concentration of at least 1 µmol/mL and "water dispersible" has a corresponding meaning. "DOPE" means 1,2-O-dioleoyl-sn-glycero-3-phosphatidylethanolamine. "DSPE" means 1,2-O-distereoyl-sn-glycero-3-phosphatidylethanolamine. "FSL-Biotin" means the water-soluble construct of the structure:

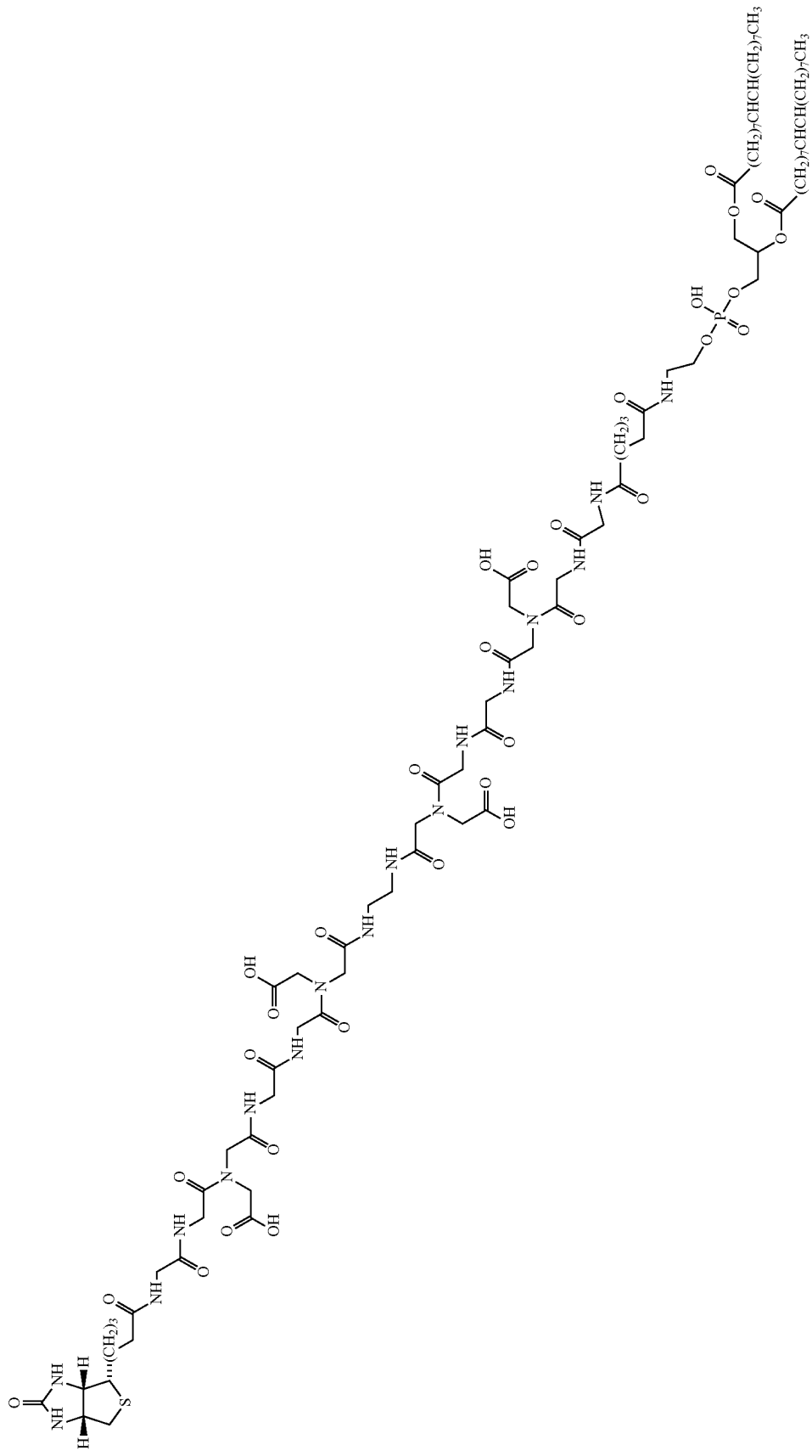

as described in the specification accompanying international application no. PCT/NZ2008/000266 (publ. no. WO 2009/048343). "FSL-A$_{tri}$" means the water-soluble construct of the structure:

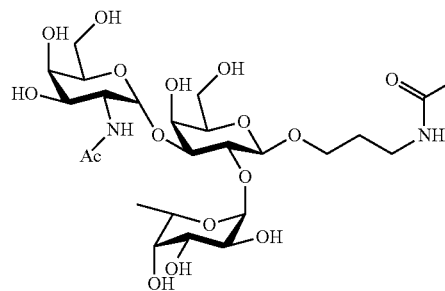
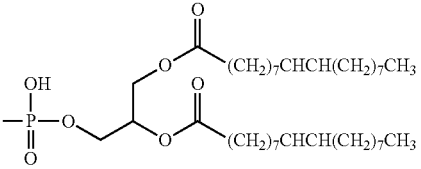

as described in the specification accompanying international application no. PCT/NZ2005/000052 (publ. no. WO 2005/090368). "Hydrophilic" means having a tendency to mix with, dissolve in, or be wetted by water; "hydrophobic" means tending to repel or fail to mix with water. "Inert" mean non-reactive under biocompatible conditions. "Kodecyte" means a cell modified by incorporation into the cell membrane of a construct of the general structure F-S-L (where F is a functional moiety, S is a spacer selected to provide a water dispersible construct and L is a lipid). "Kodevirion" means an enveloped virus particle modified by incorporation into the enveloping membrane of a construct of the general structure F-S-L (where F is a functional moiety, S is a spacer selected to provide a water dispersible construct and L is a lipid). "Localised" means associated with a surface by non-covalent interactions and "localising" and "localisation" have a corresponding meaning. "Monovalent cation" means an ion having a single positive charge and includes the monovalent cations H$^+$, Na$^+$, K$^+$ or (CH$_3$CH$_2$)$_3$N$^+$. "N$^1$-acylation" means the attachment of an acyl group (RCO—) at a terminal, primary amine of the longest chain of the molecule and "N$^1$-acylated" has a corresponding meaning. "Non-polyhydric" means the material or molecule that is the substance contains substantially no hydroxyl groups and specifically excludes substances such as cellulose and silica gel. "Non-reactive" means covalent bonds are neither broken nor formed. "PBS" denotes phosphate buffered saline. "PCV" denotes packed cell volume. "Plasma" means the colourless fluid part of blood or lymph, in which corpuscles or fat globules are suspended. "Polyamine" means an unbranched organic compound comprising three or more amine functions including at least two primary amino (—NH$_2$) functions. "Polyhydric" means the material or molecule that is the substance contains a plurality of free hydroxyl groups. "RBC" denotes red blood cell. "Saline" means a solution of one or more salts. "Serum" means the amber-coloured, protein-rich liquid which separates out when blood coagulates. "Spm" (or "spm") means spermine. "Spm-Ad-DOPE" means the water-soluble construct of the structure:

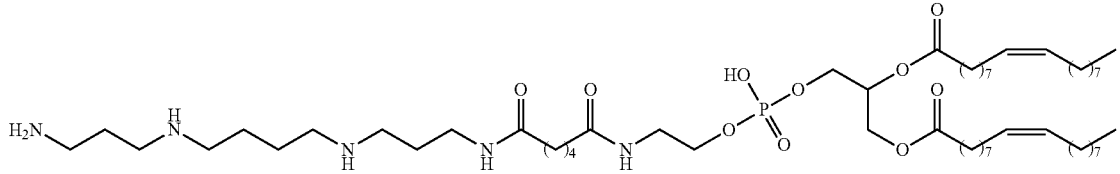

as described in the specification accompanying international application nos. PCT/NZ2015/050181 (publ. no. WO 2016/072863) and PCT/IB2016/052735 (publ. no. WO 2016/185331). "Synthetic" means prepared by chemical synthesis. "Water-soluble" means, in the context of describing the properties of a construct, that a stable, single phase system is formed in the absence of organic solvents or detergents when an amount of the construct sufficient to provide a final concentration of at least 100 µg/mL is contacted with water at a temperature of 25° C. In this context the terms "dispersible" and "soluble" are used synonymously.

It is to be understood that use of the term "non-polyhydric" as a descriptor of a substance is not intended to exclude substances that are hydrophilic. A non-polyhydric substance may be either hydrophilic or hydrophobic according to its chemical composition. Accordingly, a non-polyhydric substance may be either wettable or water repellent according to its chemical composition, but a non-polyhydric polymer will generally be inert under biocompatible conditions.

The terms "first", "second", "third", etc. used with reference to elements, features or integers of the matter defined in the Statement of Invention and Claims, or when used with reference to alternative embodiments of the invention are not intended to imply an order of preference.

Where concentrations or ratios of reagents or solvents are specified the concentration or ratio specified is the initial concentration or ratio of the reagents or solvents. Where values are expressed to one or more decimal places standard rounding applies. For example, 1.7 encompasses the range 1.650 recurring to 1.749 recurring.

In the absence of further limitation, the use of plain bonds in the representations of the structures of compounds encompasses (where applicable) the diastereomers, enantiomers and mixtures thereof of the compounds. In the representations of the structures or substructures of compounds the repeat of a divalent radical is represented by:

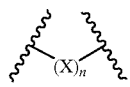

where —X— is the divalent radical repeated n times. Where the divalent radical is methylene (—CH$_2$—) the repeat of this divalent radical is represented by:

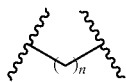

To facilitate the description of the preparation and use of the constructs the following designations are used:

"-Ad-" designates the substructure:

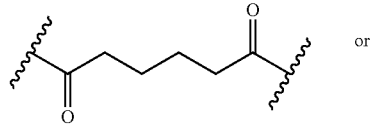 or

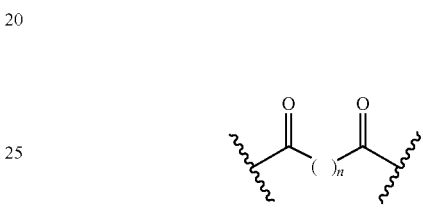

where n is the integer 4;

"—CMG(m)-" designates the substructure:

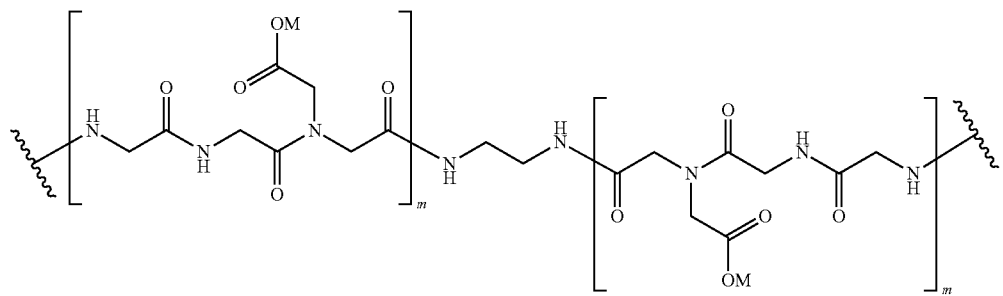

where m is the integer 1, 2, 3 or 4 and M is a monovalent substituent; and

"-DOPE" designates the substituent of the structure:

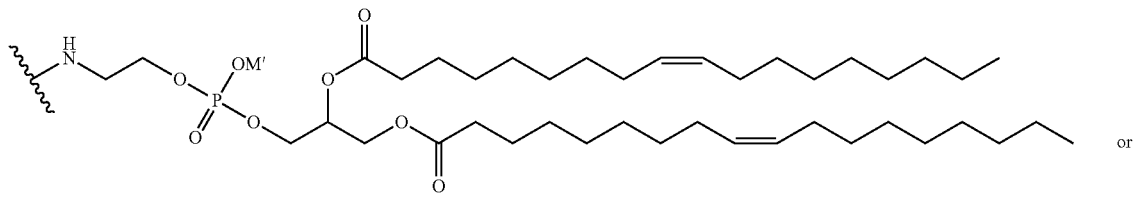 or

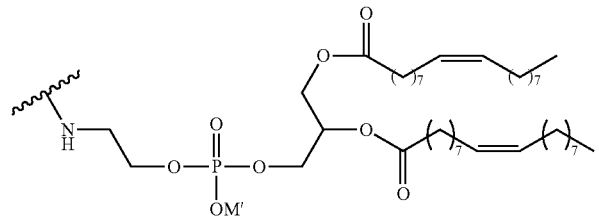

where M' is a monovalent cation (typically H).

The invention will now be described with reference to embodiments or examples and the figures of the accompanying drawings pages.

BRIEF DESCRIPTION OF DRAWINGS

FIG. 7) following mixing with a solution of avidin conjugated AlexaFlour™ 488 and examined by light (A) and fluorescent (B) microscopy.

FIG. 7) following mixing with a solution of streptavidin then FSL-Biotin kodecytes (RBCs) [20× magnification (A), 100× magnification (B)].

DETAILED DESCRIPTION

In the method of the invention a functionalising moiety is localised (as defined) to the surface of a substrate where the surface is inert (as defined). The association between the construct F-S-L comprising the functionalising moiety (F) is sufficiently strong under biocompatible (as defined) conditions to permit use in a variety of biological applications including sample analysis and preparation. These biological applications include blocking and washing steps using aqueous solutions that, save for the strength of the association between the construct and the surface of the substrate, would be expected to remove the functionalising moiety.

Figure 1:
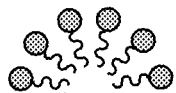
FIG. 1. Illustration of the hypothetical mechanism by which the water dispersible constructs are localised to the surface of a substrate as either a monolayer (A) or bilayer (B).
Figure 1:
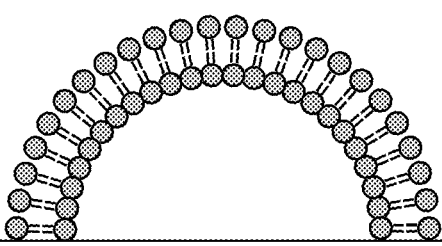
Figure 2:
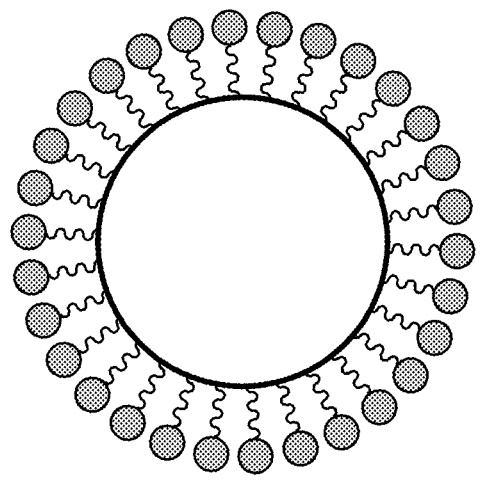
FIG. 2. Illustration of the hypothetical mechanism by which the water dispersible constructs are localised to the surface of a fibre or sphere as either a monolayer (A) or bilayer (B).
Figure 2:
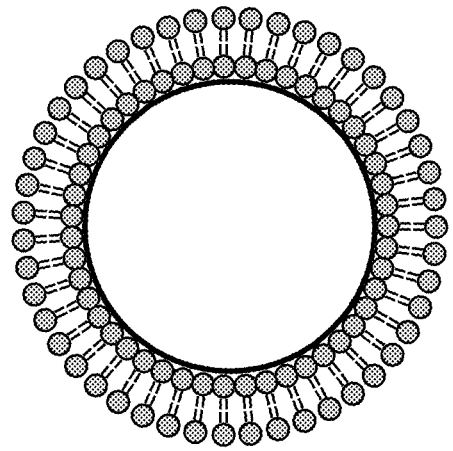

Surprisingly it has been found that the association between the construct and the surface is strong enough to be maintained during repeated washing steps irrespective of the hydrophobicity or hydrophilicity of the surface of the substrate. Without wishing to be bound by theory it is believed the strength of the association between the construct and the surface of the substrate could be attributable to the construct spontaneously forming a layer enveloping the surface of the substrate. It is suggested that such envelopment is favoured by the substrate being in the form of a fibre or thread, but this suggestion does not exclude the possibility that envelopment occurs in discrete areas of the surface of the substrate, e.g. as a lining of the inner walls of the channels present in a porous substrate, such as a filter membrane. Without wishing to be bound by theory it is hypothesised that the formation of mono- or bilayers as illustrated schematically in FIGS. 1 and 2 is thermodynamically favoured, possibly contributed to by the entropic gain attributable to the exclusion of water from the surface, thereby explaining the broad range of inert surfaces to which the method of the invention may be applied.

Products supplied under the trade name PHENEX™ (Phenomenex) are examples of polyamide (NYLON™) filter membranes. Products supplied under the trade name GH POLYPRO™ (Gelman) and the trade name METRI-CEL™ (Pall Corporation) are examples of polypropylene filter membranes. Products supplied under the trade name GELMAN TF™ (Gelman) are examples of filter membranes with a polytetrafluoroethylene (TEFLON™) surface. Despite the surface of these substrates ranging from the hydrophobic to the hydrophilic, all have been shown to be substrates capable of being functionalised according to the method of the invention. Other substrates that may be functionalised according to the method of the invention include the products supplied under the trade name DURAPOR™ (Millipore) which are filter membranes with a polyvinylidene fluoride (KYNAR™, HYLAR™) surface.

The surface of the substrate constituting a filter membrane employed in the analysis and preparation of biological samples, such as plasma and serum, is purposefully selected to be antifouling. The antifouling properties prevent, or at least substantially mitigate, non-specific binding of components of the biological samples to the membrane. The avoidance of non-specific binding to the filter membrane is desirable to avoid clogging of the membrane and cross-contamination of biological samples with repeated use. The antifouling characteristic of the surface of the substrate constituting a filter membrane necessarily limits the ability to introduce functionalities that promote selective binding of minor components of the biological sample to the membrane and consequential concentration in situ or following elution.

The method of the invention permits the functionalization of a surface that has purposefully been selected to be antifouling. The functionalization is achieved by the localisation of the functionalising moiety to the surface under conditions that are biocompatible and do not affect the structural integrity of the substrate. Use of the method of the invention enables novel sample analysis and preparation procedures to be employed as illustrated with reference to the Figures of the accompanying drawings and the following examples.

EXAMPLE 1

Dispersions of the aminopropyl derivative of blood group A trisaccharide (A$_{tri}$-S$_1$) and the construct A$_{tri}$-sp-Ad-DOPE (FSL-A) were prepared at a concentration of 0.2 mM in PBS containing 0.01% polyoxyethylene (20) sorbitan monolaureate (TWEEN™ 20) and 1% inkjet ink (magenta).

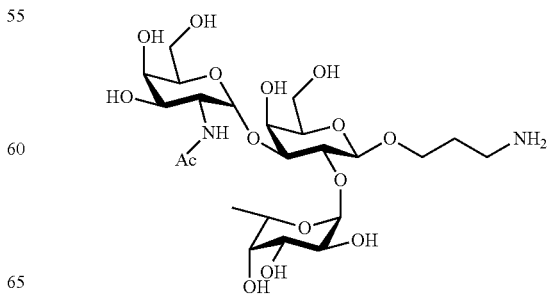

A$_{tri}$-S$_1$ (as Described in the Specification Accompanying International Application No. PCT/NZ2005/000052 (Publ. No. WO 2005/090368))

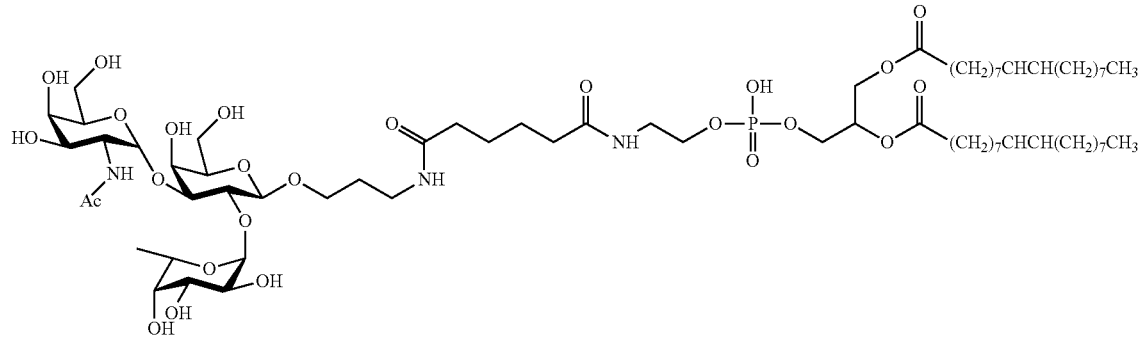

FSL-A (as Described in the Specification Accompanying International Application No. PCT/NZ2005/000052 (Publ. No. WO 2005/090368))

Figure 3:
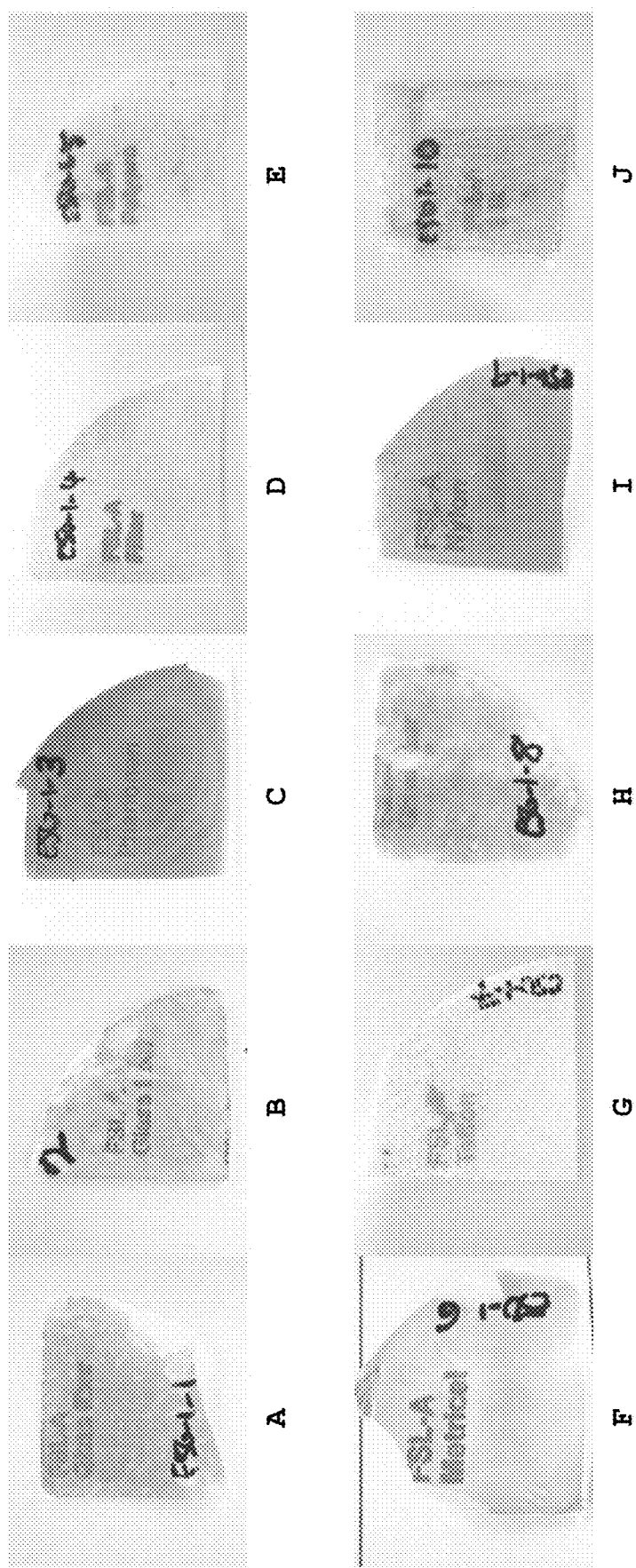
FIG. 3. Appearance of the surface of substrates following printing and immunostaining using a 1 in 5 dilution in BSA of anti-A immunoglobulin (EPICLONE™ monoclonal, CSL Limited) according to the method described in Example 1: A—glass fibre filter paper GC-50 (Advanetc); B—glass microfiber filter GF/B (Whatman); C—nylon membrane filter 0.2 μm (Phenomenex); D—filter paper 1 (Whatman); E—polypropylene filter membrane (Gelman Sciences); F—METRICEL™ filter membrane GA-3 1.2 μm (Gelman Sciences); G—TEFLON™ filter membrane TF-200 0.2 μm (Gelman Instrument Company); H—glass fibre filter A/E (Pall Life Sciences), I—nylon 66 filter membrane 0.45 μm (Schleicher & Schuell) and J—silk.
Figure 4:
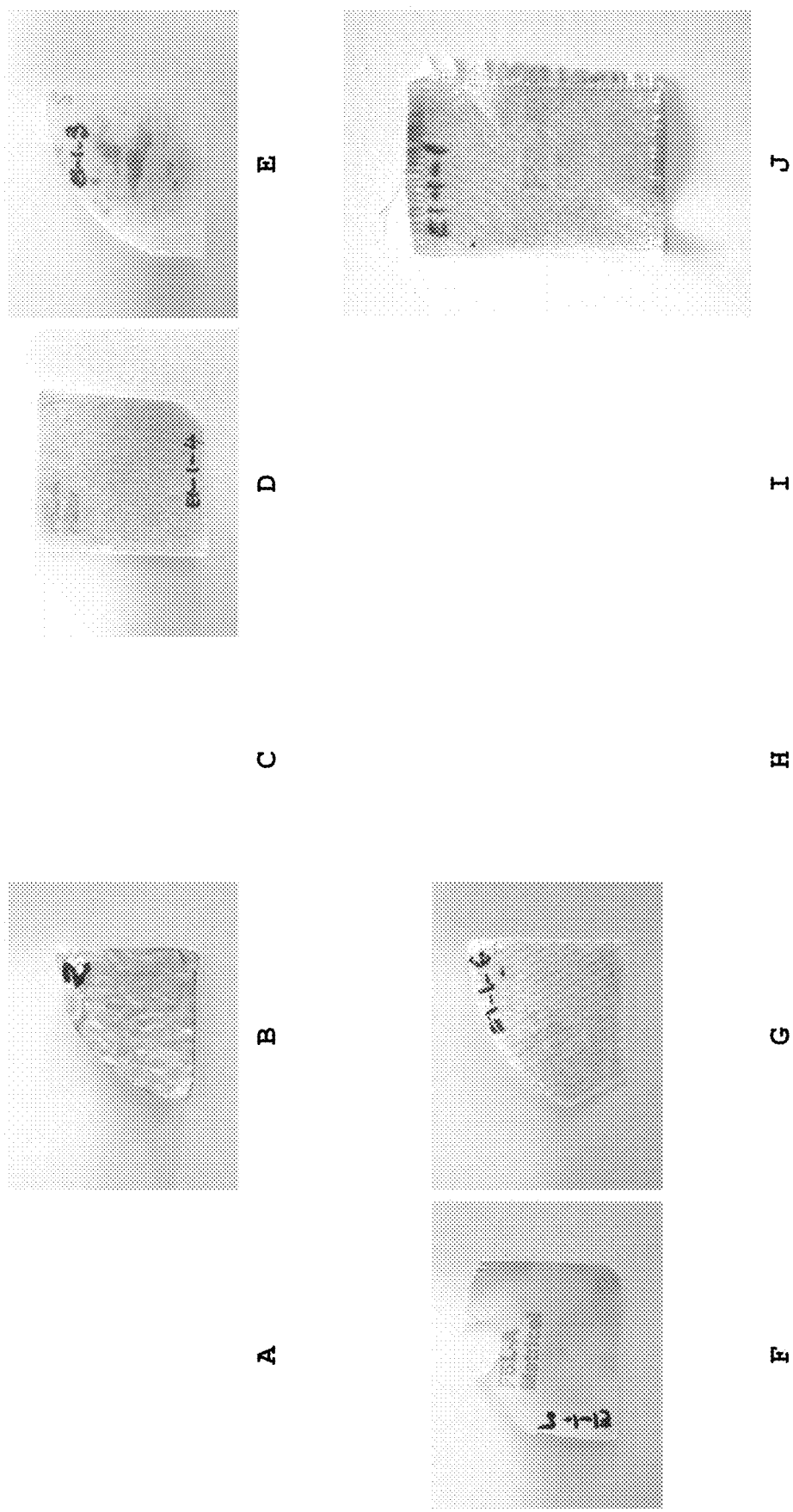
FIG. 4. Appearance of the surface of substrates following printing and immunostaining using a 1 in 2 dilution in BSA of O group serum according to the method described in Example 1: B—glass microfiber filter GF/B (Whatman); D—filter paper 1 (Whatman); E—polypropylene filter membrane (Gelman Sciences); F—METRICEL™ filter membrane GA-3 1.2 μm (Gelman Sciences); G—TEFLON™ filter membrane TF-200 0.2 μm (Gelman Instrument Company); and J—silk.

The dispersions were loaded into separate ink cartridges of an EPSON STYLUS™ T21 piezoelectric inkjet printer. The identity of the dispersion and substrate were printed onto samples of the following substrates: glass fibre filter paper GC-50 (Advanetc); glass microfiber filter GF/B (Whatman); nylon membrane filter 0.2 μm (Phenomenex); filter paper 1 (Whatman); polypropylene filter membrane (Gelman Sciences); METRICEL™ filter membrane GA-3 1.2 μm (Gelman Sciences); TEFLON™ filter membrane TF-200 0.2 μm (Gelman Instrument Company); glass fibre filter A/E (Pall Life Sciences), nylon 66 filter membrane 0.45 μm (Schleicher & Schuell) and silk. The printed samples of substrate were then immersed in a solution of 2% (w/v) bovine serum albumin (BSA) in PBS for 1 hour prior to being rinsed and the surface of the substrate being flooded with a 1 in 5 dilution in BSA of anti-A immunoglobulin (EPICLONE™ monoclonal, CSL Limited) and incubated for 30 minutes, or flooded with a 1 in 2 dilution in BSA of O group serum and incubated for 1 hour. The surfaces of the substrates were then washed 6 times with PBS prior to being flooded with a 1:400 dilution of alkaline phosphatase conjugated sheep anti-mouse immunoglobulin (Chemicon) and incubated for 30 minutes. The surfaces of the substrates were then washed 6 times with PBS followed by a washing of substrate buffer (100 mM Tris, 100 mM NaCl, 50 mM MgCl$_2$, pH 9.5). The substrate buffer washed surfaces of the substrates were then flooded with a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt)(NBTC-BCIP) in 67% DMSO (Roche)) for about 10 minutes. The chromogenic reaction was stopped by rinsing the surface of each substrate with deionised water. The appearance of the surface of each substrate following incubation with the chromogenic substrate is provided in FIG. 3 and FIG. 4. It will be observed that there was no immunostaining of the surface of the substrate in the region where the aminopropyl derivative of the A trisaccharide (A$_{tri}$-sp-NH$_2$) was printed. It is assumed that the aminopropyl derivative of the A trisaccharide (A$_{tri}$-sp-NH$_2$) was washed away during the immunostaining procedure.

EXAMPLE 2

Dispersions of the construct B$_{tri}$-sp-Ad-DOPE (FSL-B) and its monoacyl counterpart (monoacyl-B) were prepared at a concentration of 0.4 mM in PBS containing 0.01% polyoxyethylene (20) sorbitan monolaureate (TWEEN™ 20) and 1% inkjet ink (magenta).

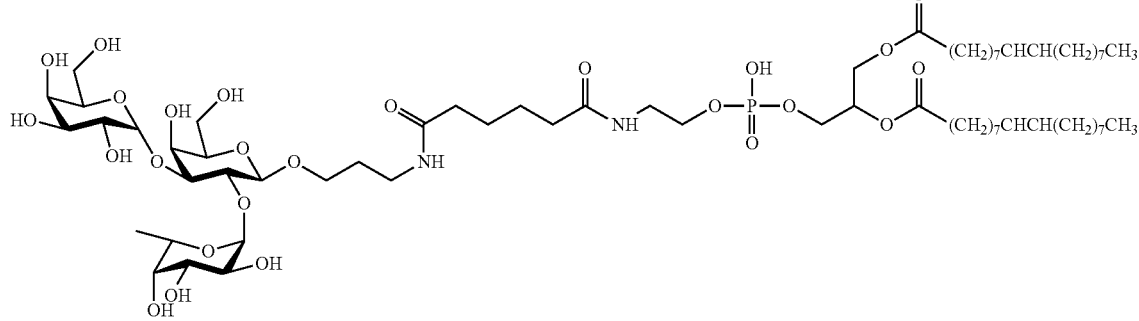

FSL-B (as Described in the Specification Accompanying International Application No. PCT/NZ2005/000052 (Publ. No. WO 2005/090368))

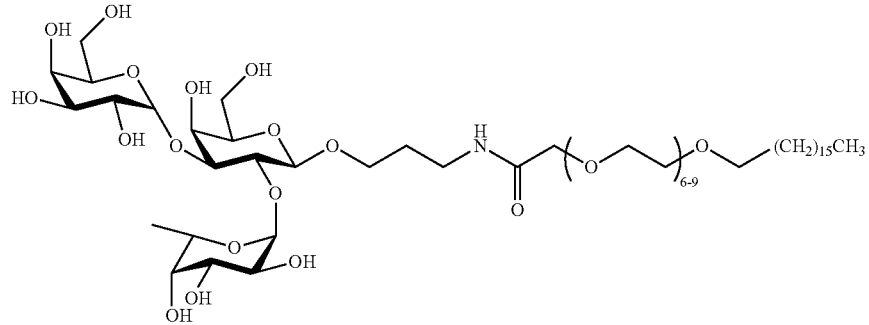

Monoacyl-B (as Described in the Specification Accompanying International Application No. PCT/NZ2005/000052 (Publ. No. WO 2005/090368)

Figure 5:
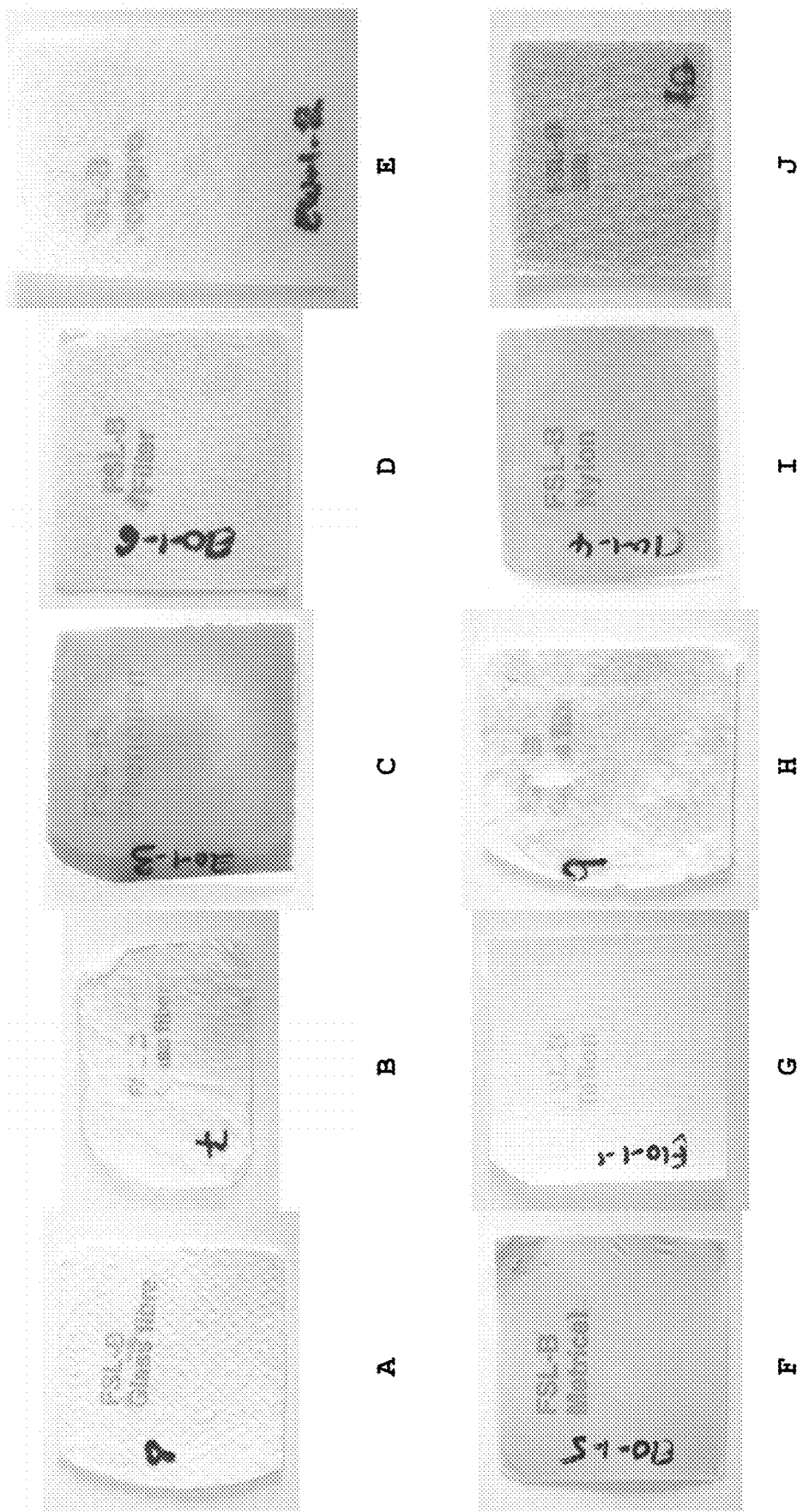
FIG. 5. Appearance of the surface of substrates following printing and immunostaining using a 1 in 5 dilution in BSA of anti-B immunoglobulin (EPICLONE™ monoclonal, CSL Limited) according to the method described in Example 2: A—glass fibre filter paper GC-50 (Advanetc); B—glass microfiber filter GF/B (Whatman); C—nylon membrane filter 0.2 μm (Phenomenex); D—filter paper 1 (Whatman); E—polypropylene filter membrane (Gelman Sciences); F—METRICEL™ filter membrane GA-3 1.2 μm (Gelman Sciences); G—TEFLON™ filter membrane TF-200 0.2 μm (Gelman Instrument Company); H—glass fibre filter A/E (Pall Life Sciences), I—nylon 66 filter membrane 0.45 μm (Schleicher & Schuell) and J—silk.

The dispersions were loaded into separate ink cartridges of an EPSON STYLUS™ T21 piezoelectric inkjet printer. The identity of the dispersion and substrate were printed onto samples of the following substrates: glass fibre filter paper GC-50 (Advanetc); glass microfiber filter GF/B (Whatman); nylon membrane filter 0.2 μm (Phenomenex); filter paper 1 (Whatman); polypropylene filter membrane (Gelman Sciences); METRICEL™ filter membrane GA-3 1.2 μm (Gelman Sciences); TEFLON™ filter membrane TF-200 0.2 μm (Gelman Instrument Company); glass fibre filter A/E (Pall Life Sciences), nylon 66 filter membrane 0.45 μm (Schleicher & Schuell) and silk. The printed samples of substrate were then immersed in a solution of 2% (w/v) bovine serum albumin (BSA) in PBS for 1 hour prior to being rinsed and the surface of the substrate being flooded with a 1 in 5 dilution in BSA of anti-B immunoglobulin (EPICLONE™ monoclonal, CSL Limited) and incubated for 30 minutes. The surfaces of the substrates were then washed 6 times with PBS prior to being flooded with a 1:400 dilution of alkaline phosphatase conjugated sheep anti-mouse immunoglobulin (Chemicon) and incubated for 30 minutes. The surfaces of the substrates were then washed 6 times with PBS followed by a washing of substrate buffer (100 mM Tris, 100 mM NaCl, 50 mM $MgCl_2$, pH 9.5). The substrate buffer washed surfaces of the substrates were then flooded with a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt)(NBTC-BCIP) in 67% DMSO (Roche)) for about 10 minutes. The chromogenic reaction was stopped by rinsing the surface of each substrate with deionised water. The appearance of the surface of each substrate following incubation with the chromogenic substrate is provided in FIG. 5. It will be observed that there was no immunostaining of the surface of the substrate in the region where the monoacyl counterpart (monoacyl-B) of the construct $B_{tri}$-sp-Ad-DOPE (FSL-B) was printed. It is assumed that the monoacyl counterpart was washed away during the immunostaining procedure.

EXAMPLE 3

Dispersions of the constructs FSL-A and FSL-Biotin at a concentration of 0.5 mg/ml (circa 6 mM) in PBS were painted onto glass fibre threads using a brush. The painted thread was allowed to dry between applications of subsequent layers.

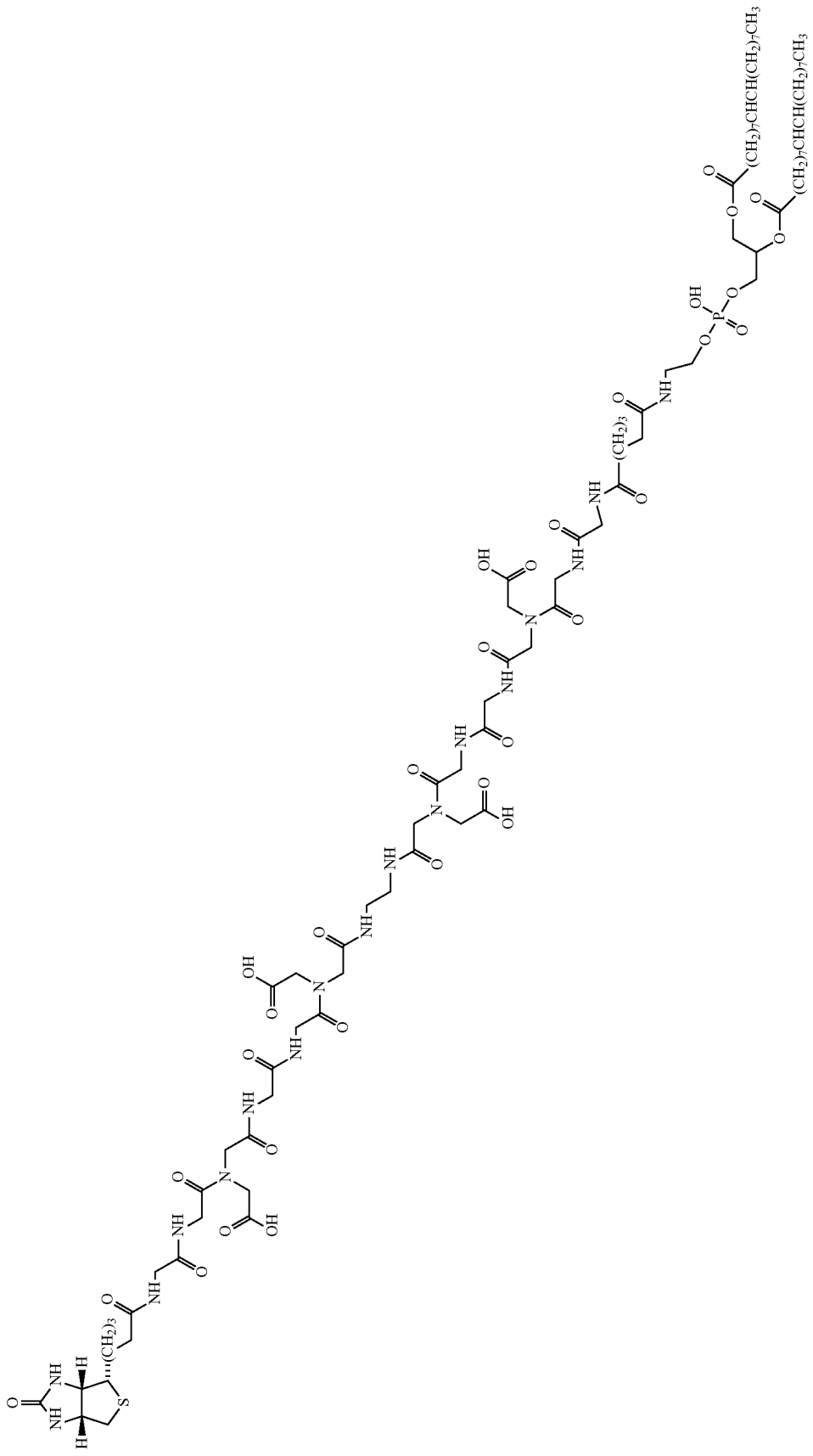

FSL-Biotin (as Described in the Specification Accompanying International Application No. PCT/NZ2008/000266 (Publ. No. WO 2009/048343))

Figure 6:
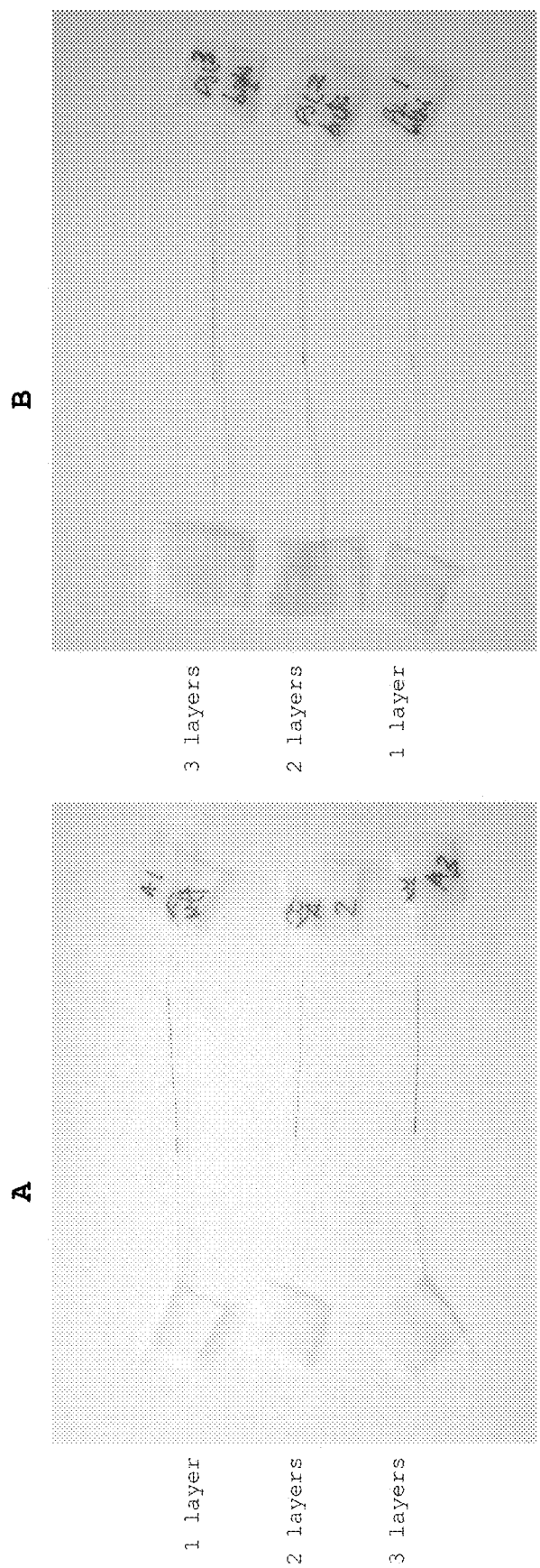
FIG. 6. Appearance of fibre glass threads painted with layers of FSL-A and FSL-Biotin following immunostaining according to the method described in Example 3. The left hand end of the thread has not been painted.

A glass fibre thread painted with 1 to 3 layers of the dispersion of FSL-A was immersed in a solution of 2% (w/v) bovine serum albumin (BSA) in PBS for 1 hour prior to being rinsed and immersed in a 1 in 5 dilution in BSA of anti-B immunoglobulin (EPICLONE™ monoclonal, CSL Limited) for 30 minutes. The painted glass fibre thread was then washed 6 times with PBS prior to being immersed in a 1:400 dilution of alkaline phosphatase conjugated sheep anti-mouse immunoglobulin (Chemicon) for 30 minutes. The thread was then washed 6 times with PBS followed by a washing of substrate buffer (100 mM Tris, 100 mM NaCl, 50 mM $MgCl_2$, pH 9.5). The washed thread was then immersed in a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt)(NBTC-BCIP) in 67% DMSO (Roche)) for about 10 minutes. The chromogenic reaction was stopped by immersing the thread in deionised water. The appearance of threads coated with 1, 2 or 3 layers of FSL-A following incubation with the chromogenic substrate is provided in FIG. 6A.

A glass fibre thread painted with 1 to 3 layers of the dispersion of FSL-Biotin was immersed in a solution of 2 µg/mL streptavidin-alkaline phosphatase conjugate in bovine serum albumin (BSA) in PBS for 1 hour prior to being washed 6 times with PBS followed by a washing of substrate buffer (100 mM Tris, 100 mM NaCl, 50 mM $MgCl_2$, pH 9.5). The washed thread was then immersed in a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt)(NBTC-BCIP) in 67% DMSO (Roche)) for about 15 minutes. The chromogenic reaction was stopped by immersing the thread in deionised water. The appearance of threads coated with 1, 2 or 3 layers of FSL-Biotin following incubation with the chromogenic substrate is provided in FIG. 6B.

Figure 7:
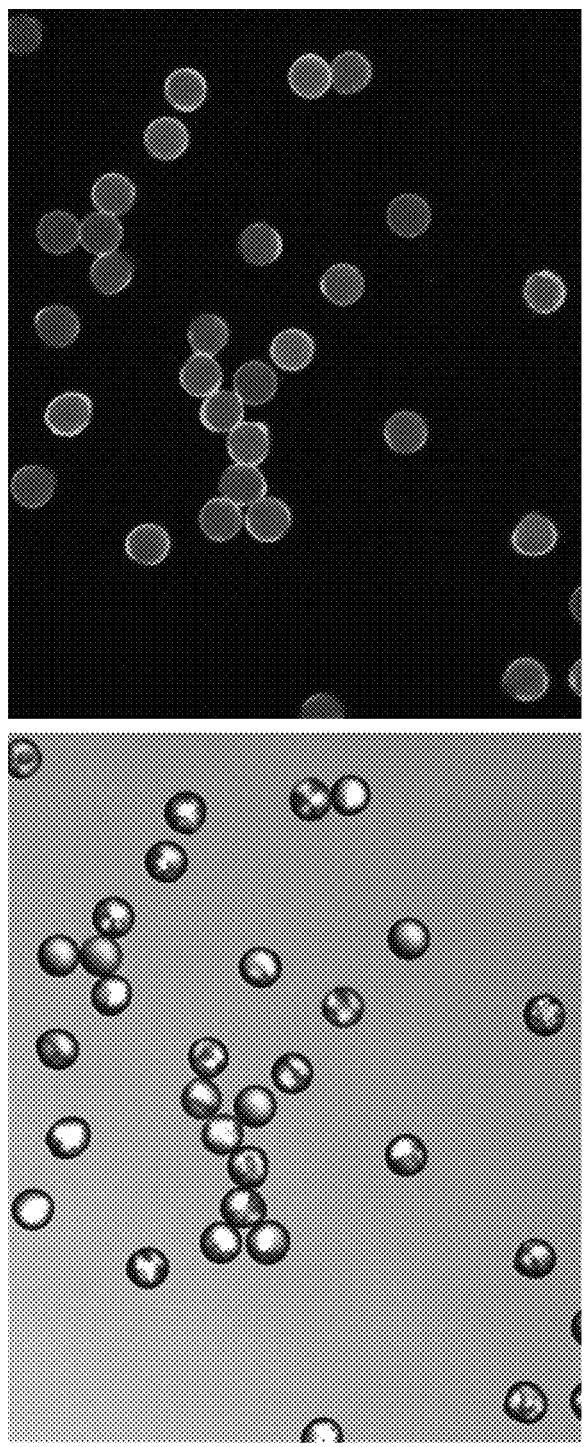
FIG. 7. Photomicrographs of functionalised polycarbonate microspheres (the surface of which has been functionalised using the construct designated FSL-Biotin) following mixing with a solution of avidin conjugated AlexaFlour™ 488 and examined by light (A) and fluorescent (B) microscopy.
Figure 8:
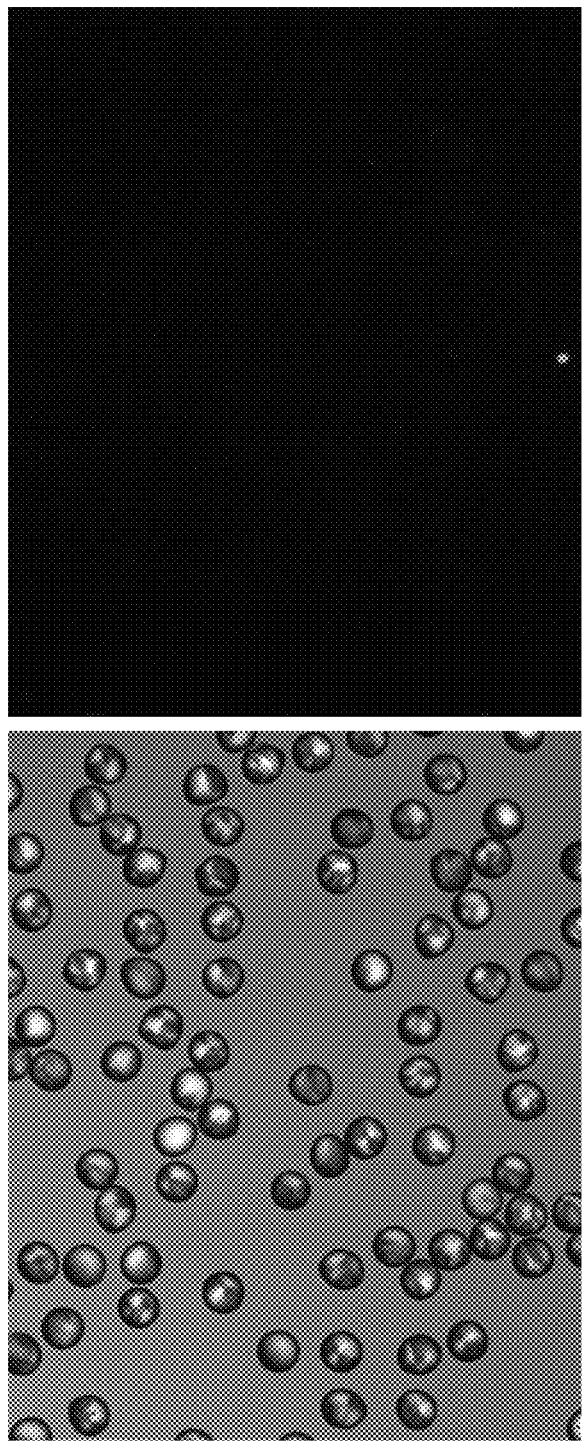
FIG. 8. Photomicrographs of untreated (control) polycarbonate microspheres (cf.
Figure 9:
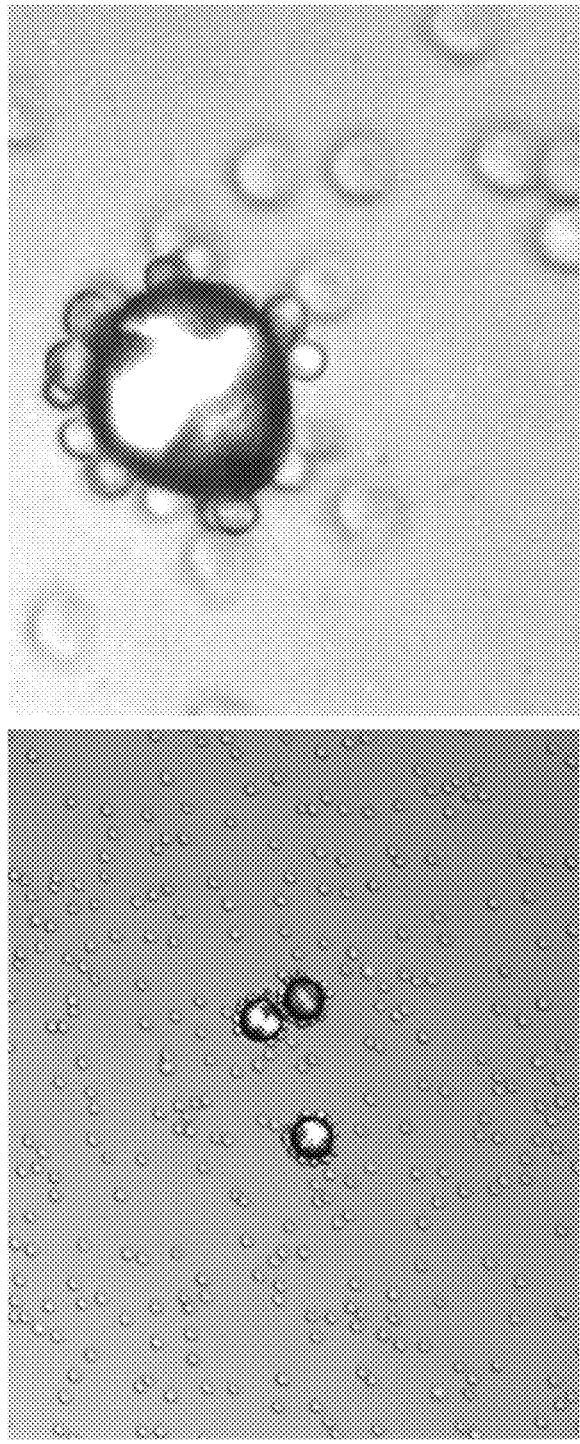
FIG. 9. Photomicrographs of functionalised polycarbonate microspheres (the surface of which has been functionalised using the construct designated FSL-Biotin) following mixing with a solution of streptavidin then FSL-Biotin kodecytes (RBCs) [20× magnification (A), 100× magnification (B)].

The ability to functionalise the otherwise inert surface of a substrate allows a number of novel applications to be developed. For example, immunosorbent assays may be performed with greater facility using laboratory filter assemblies such as those illustrated in cross section in FIG. 7. It will be appreciated by those skilled in the art that the separate steps of an immunosorbent assay as described in Examples 1, 2 and 3 could be readily performed in such a filter assembly using the method of the invention.

EXAMPLE 4

Localising Functional Moieties to the Surface of Monodisperse Polycarbonate Microspheres An aliquot (2 to 3 µL) of polycarbonate microspheres (MAKROLON™ 2808, Nanomi B.V.) of uniform diameter (20 µM±3%) (monodisperse) was mixed with a 30 µL volume of a 500 µg/mL dispersion in PBS of the construct designated FSL-Biotin. The mixture was incubated at room temperature (circa 22° C.) for 30 minutes prior to washing of the microspheres by repeated (three times) centrifugation and resuspension in PBS. The functionalised and washed microspheres were finally resuspended in a volume of 200 µL of PBS. An aliquot (2 to 3 µL) of the same polycarbonate microspheres were also suspended in a volume of 200 µL of PBS without prior mixing with a dispersion of construct and used as a control.

A 50 µL volume of the suspension of functionalised and washed microspheres was mixed with a 50 µL volume of a 100 µg/mL solution in PBS of avidin conjugated Alexa-Flour™ 488 (Life Technologies). Similarly, a 50 µL volume of the suspension of untreated (control) polycarbonate microspheres was mixed with a 50 µL volume of a 100 µL/mL solution in PBS of avidin conjugated AlexaFlour™ 488 (Life Technologies). Both mixtures were incubated at 37° C. for 30 minutes prior to washing of the microspheres by repeated (three times) centrifugation and resuspension in PBS as before. The washed microspheres were resuspended in a volume of PBS sufficient to permit examination by light and fluorescence microscopy. Only the functionalised microspheres were observed to fluoresce (see FIG. 7 and FIG. 7).

EXAMPLE 5

Localising RBCs to the Surface of Monodisperse Polycarbonate Microspheres Via Avidin-Biotin Conjugation Biotin was localised to the surface of O-group RBCs using the construct designated FSL-Biotin. A 50 µL volume of packed RBCs was mixed with a 50 µL volume of a 200 µg/mL dispersion of PBS of the construct. The mixture was incubated at 37° C. for 2 hours prior to washing of the cells by repeated (three times) centrifugation and resuspension in PBS. The washed and modified RBCs (kodecytes) were finally resuspended in a volume of PBS at a density of 20% of the PCV.

An aliquot (2 to 3 µL) of polycarbonate microspheres (MAKROLON™ 2808, Nanomi B.V.) of uniform diameter (20 µM±3%) (monodisperse) was mixed with a 30 µL volume of a 200 µg/mL dispersion in PBS of the construct designated FSL-Biotin. The mixture was incubated at room temperature (circa 22° C.) for 30 minutes prior to washing of the functionalised microspheres by repeated (three times) centrifugation and resuspension in PBS. The functionalised and washed microspheres were finally resuspended in a volume of 200 µL of PBS.

A 50 µL volume of the suspension of the functionalised and washed microspheres was mixed with a 50 µL volume of a 200 µg/mL solution in PBS of streptavidin and the mixture incubated at room temperature (circa 22° C.) for 30 minutes. Following incubation the avidinylated functionalised microspheres were washed by repeated (three times) centrifugation and resuspension in PBS.

Figure 10:
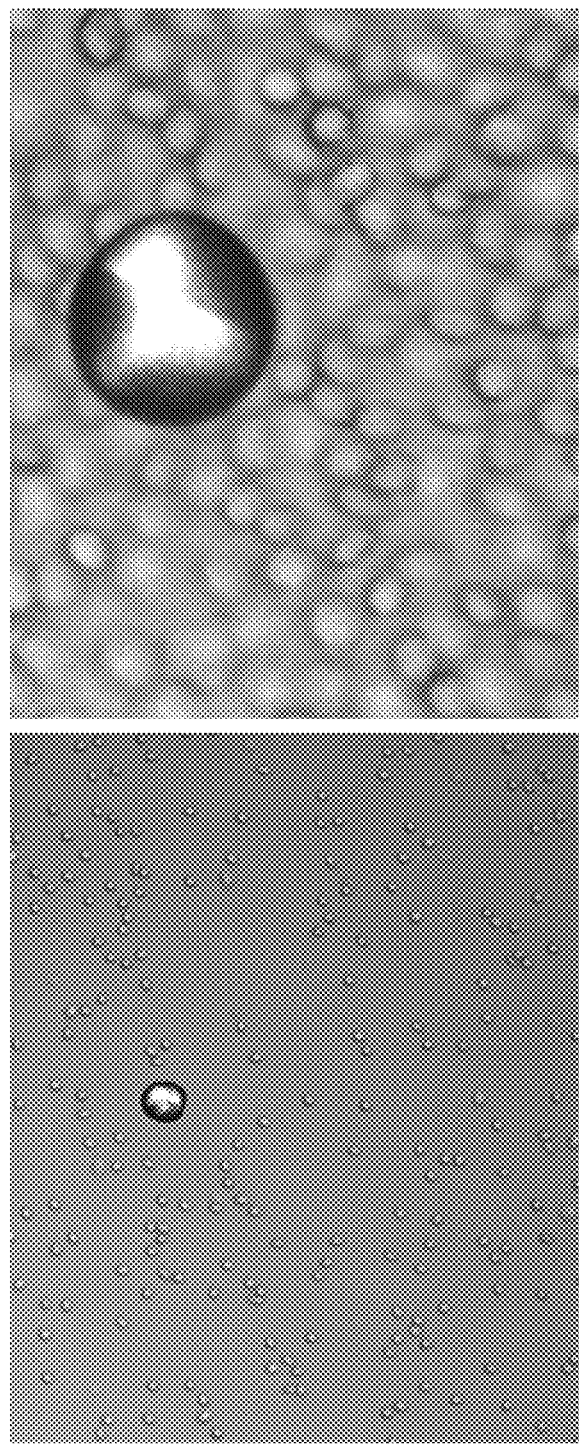
FIG. 10. Photomicrographs of untreated (control) polycarbonate microspheres (cf.
Figure 11:
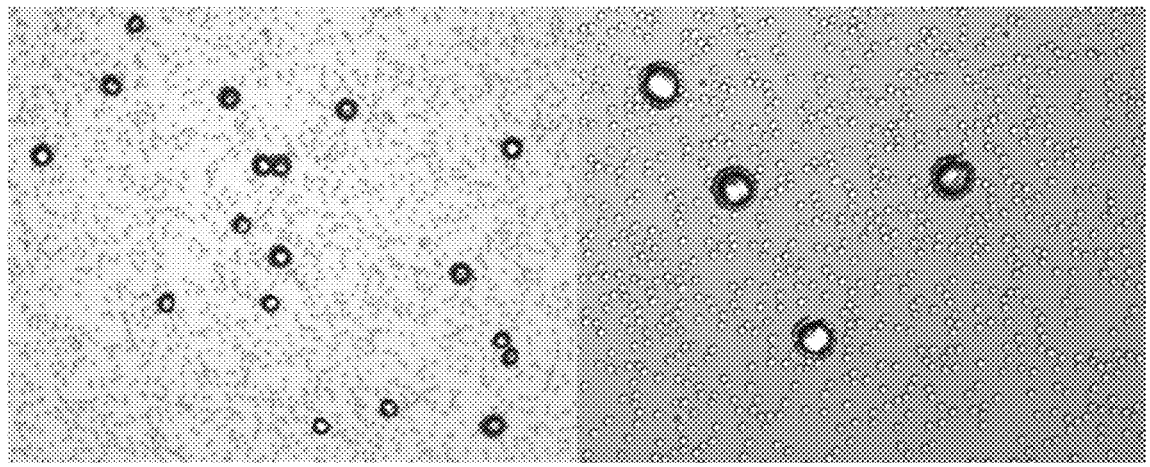
FIG. 11. Photomicrographs of functionalised polycarbonate microspheres (the surface of which has been functionalised using the construct designated FSL-A$_{tri}$) following mixing with a solution of monoclonal anti-A (Epiclone, CSL Limited) then FSL-A$_{tri}$ kodecytes (RBCs) [10× magnification (A), 20× magnification (B), 100× magnification, first focal plane (C), 100× magnification, second focal plane (D)].
Figure 11:
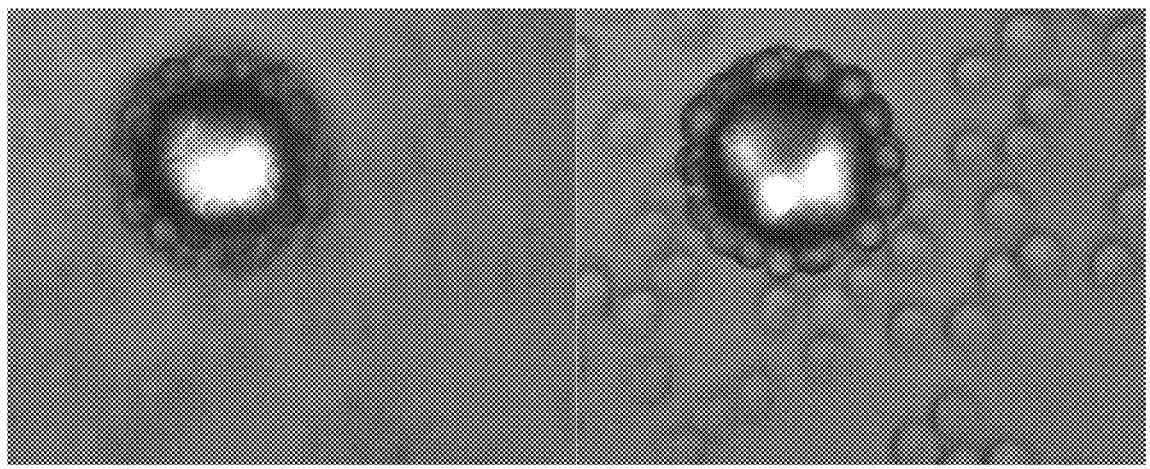

A 50 µL volume of the FSL-Biotin kodecytes suspended in PBS at a density of 20% PCV was mixed with a 20 µL volume of the suspension of avidinylated functionalised microspheres. A 20 µL volume of O-group RBCs resuspended in PBS at a density of 20% PCV was mixed with a 20 µL volume of the avidinylated functionalised microspheres as a control. Both mixtures were incubated at 37° C. for 1½ hours before dilution with 100 µL PBS to permit viewing by light microscopy. FSL-Biotin kodecytes were observed to be localised to the surface of the avidinylated functionalised microspheres only (see FIG. 10 and FIG. 11).

EXAMPLE 6

Localising RBCs to the Surface of Monodisperse Polycarbonate Microspheres Via Antibody-Antigen Cross-Reactivity Blood group A-antigen ($A_{tri}$) was localised to the surface of O-group RBCs using the construct designated FSL-$A_{tri}$. A 50 µL volume of the packed RBCs was mixed with a 50 µL volume of a 200 µg/mL dispersion in PBS of the construct. The mixture was incubated at 37° C. for 2 hours prior to washing of the cells by repeated (three times) centrifugation and resuspension in PBS. The washed and modified RBCs (kodecytes) were finally resuspended in a volume of PBS at a density of 20% of the PCV.

An aliquot (2 to 3 µL) of polycarbonate microspheres (MAKROLON™ 2808, Nanomi B.V.) of uniform diameter (20 µM±3%) (monodisperse) was mixed with a 30 µL volume of a 200 µg/mL dispersion in PBS of the construct designated FSL-$A_{tri}$. The mixture was incubated at room temperature (circa 22° C.) for 30 minutes prior to washing of the functionalised microspheres by repeated (three times) centrifugation and resuspension in PBS. The functionalised and washed microspheres were finally resuspended in a volume of 200 µL of PBS.

A 50 µL volume of the suspension of the functionalised and washed microspheres was mixed with a 50 µL volume of undiluted monoclonal anti-A (Epiclone, CSL Limited) and the mixture incubated at room temperature (circa 22° C.) for 60 minutes. Following incubation the antibody bound functionalised microspheres were washed by repeated (three times) centrifugation and resuspended in PBS.

A 20 µL volume of the suspension of FSL-$A_{tri}$ kodecytes resuspended in PBS at a density of 20% PCV was mixed with a 20 µL volume of the antibody bound functionalised microspheres. A 20 µL volume of O-group RBCs resuspended in PBS at a density of 20% PCV was mixed with a 20 µL volume of the suspension of the antibody bound functionalised microspheres as a first control. A 20 µL volume of the suspension of FSL-$A_{tri}$ kodecytes resuspended in PBS at a density of 20% PCV was mixed with a 20 µL volume of the functionalised microspheres obtained prior to mixing and incubation with the undiluted monoclonal anti-A (Epiclone, CSL Limited) as a second control. All mixtures were incubated at room temperature (circa 22° C.) for 1½ hours before dilution by the addition of a 200 µL volume of PBS to permit viewing by light microscopy.

Figure 12:
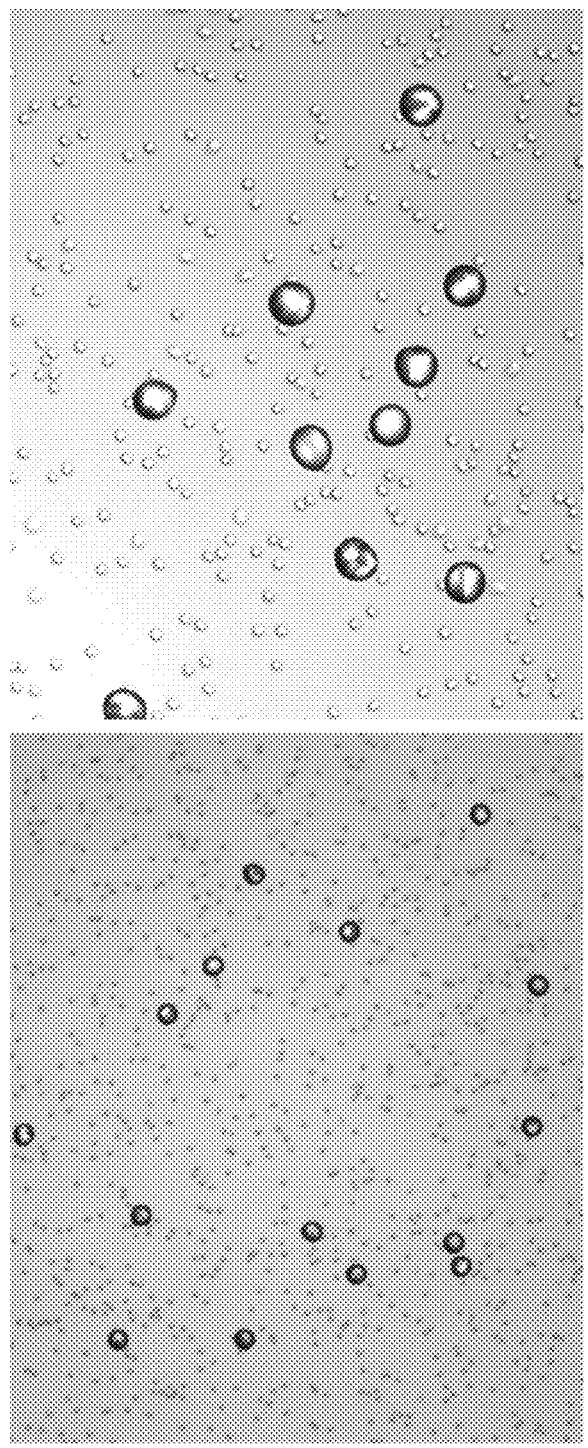
FIG. 12. Photomicrographs of functionalised polycarbonate microspheres (the surface of which has been functionalised using the construct designated FSL-A$_{tri}$) following mixing with a solution of monoclonal anti-A (Epiclone, CSL Limited) then O-group RBCs [10× magnification (A), 20× magnification (B)].
Figure 13:
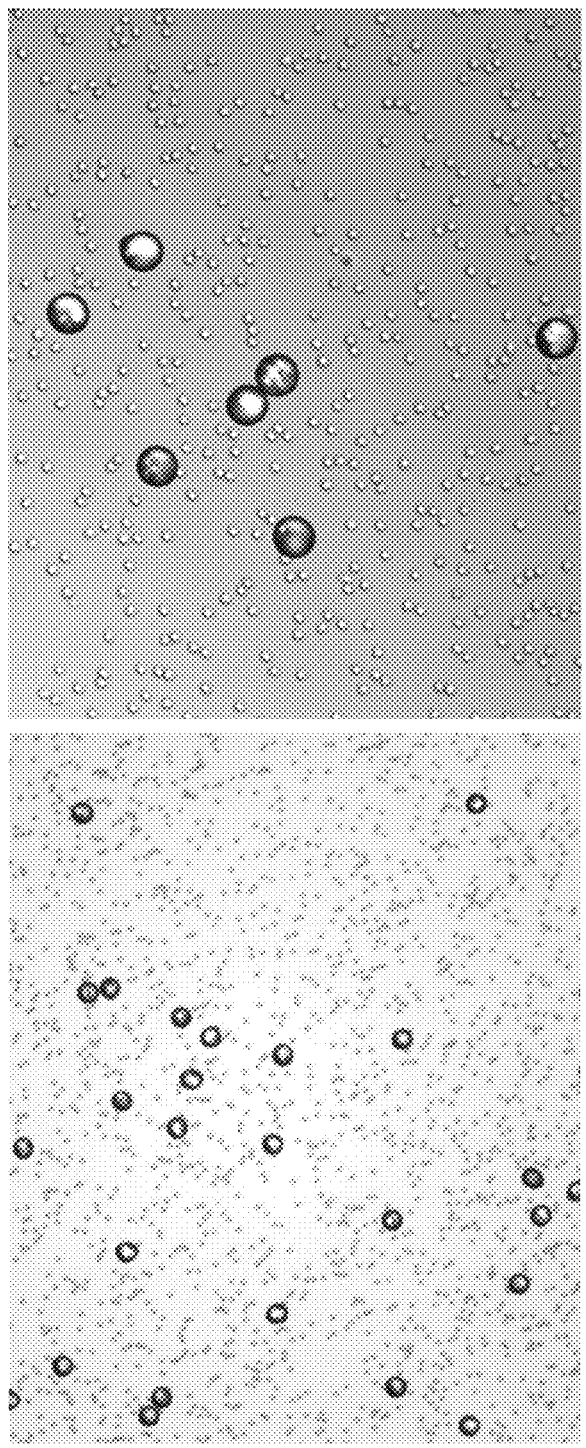
FIG. 13. Photomicrographs of functionalised polycarbonate microspheres (the surface of which has been functionalised using the construct designated FSL-A$_{tri}$) following mixing with FSL-A$_{tri}$ kodecytes (RBCs) in the absence of monoclonal anti-A (Epiclone, CSL Limited) [10× magnification (A), 20× magnification (B)].
Figure 14:
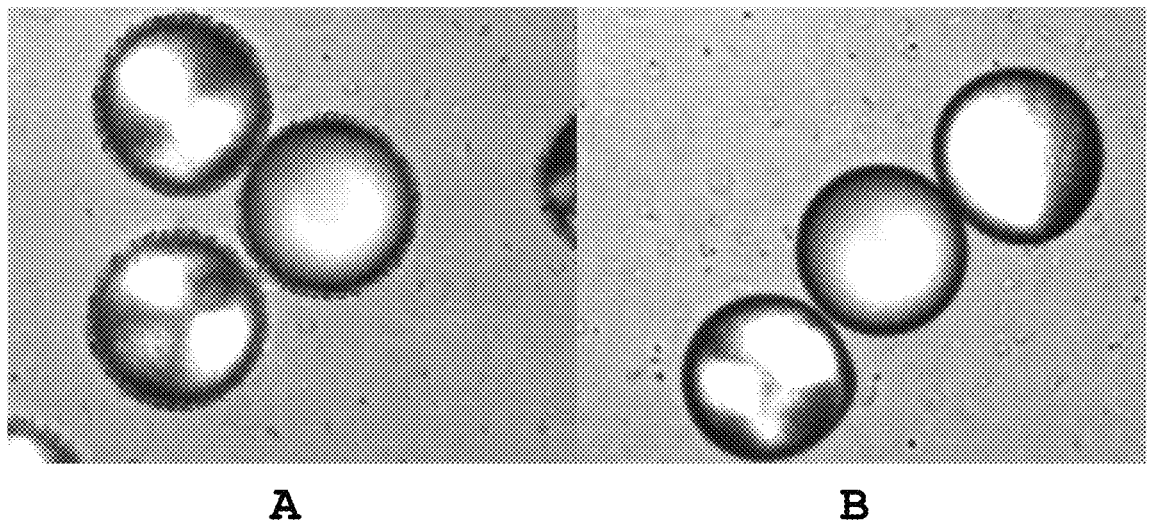
FIG. 14. Photomicrographs of functionalised polycarbonate microspheres (the surface of which has been functionalised using the construct designated FSL-Biotin) (A) and untreated (control) polycarbonate microspheres (B) following mixing with FSL-A$_{tri}$ bacteria (*Staphylococcus sarophyticus*).

RBCs were observed to be localised to the surface of the treated and washed polycarbonate microspheres only where antibody was present (see FIG. 12, FIG. 13 and FIG. 14).

EXAMPLE 7

Localising Bacteria to the Surface of Monodisperse Polycarbonate Microspheres Via Avidin-Biotin Conjugation Biotin was localised to the surface of two species of bacterium (*Staphylococcus sarophyticus* and *Micrococcus luteus*) using the construct designated FSL-Biotin. A 50 µL volume of a 200 µg/mL dispersion in PBS of the construct was mixed with a colony of each bacterium. Each mixture was incubated at 37° C. for 2 hours prior to washing of the bacterial cells by repeated (three times) centrifugation and resuspension in PBS. The washed and treated bacterial cells were finally resuspended in a 300 µL volume of PBS.

An aliquot (2 to 3 µL) of polycarbonate microspheres (MAKROLON™ 2808, Nanomi B.V.) of uniform diameter (20 µM±3%) (monodisperse) was mixed with a 30 µL volume of a 200 µg/mL dispersion in PBS of the construct designated FSL-Biotin. The mixture was incubated at room temperature (circa 22° C.) for 30 minutes prior to washing of the functionalised microspheres by repeated (three times) centrifugation and resuspension in PBS. The functionalised microspheres were finally resuspended in a volume of 200 µL of PBS. A 50 µL volume of the functionalised microspheres was mixed with a 50 µL volume of a 2 mg/mL solution in PBS of avidin and the mixture incubated at room temperature (circa 22° C.) for 30 minutes. Following incubation the avidinylated functionalised microspheres were washed by repeated (three times) centrifugation and resuspension in PBS.

Figure 15:
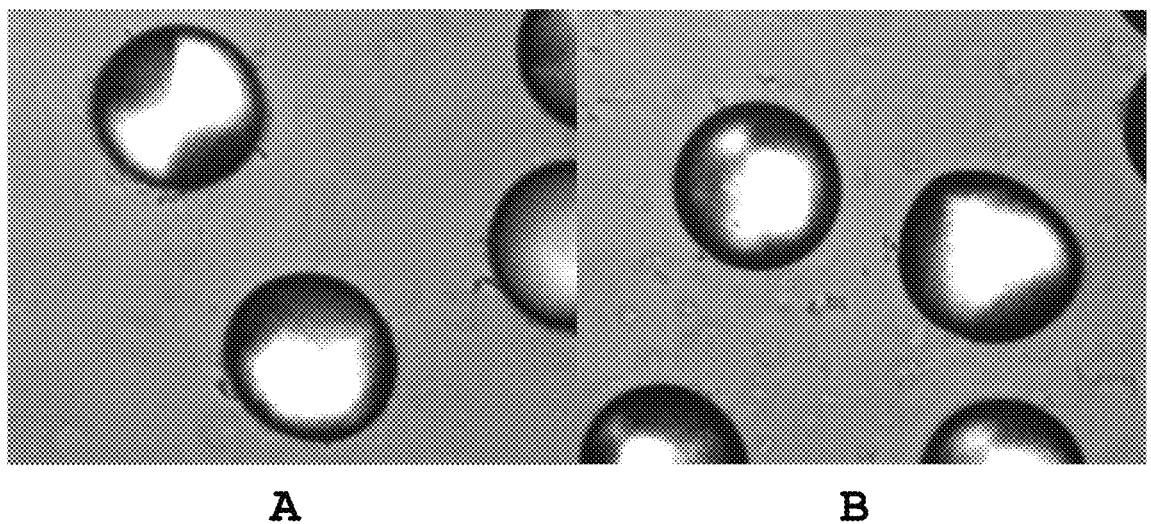
FIG. 15. Photomicrographs of functionalised polycarbonate microspheres (the surface of which has been functionalised using the construct designated FSL-Biotin) (A) and untreated (control) polycarbonate microspheres (B) following mixing with FSL-A$_{tri}$ bacteria (*Micrococcus luteus*).
Figure 16:
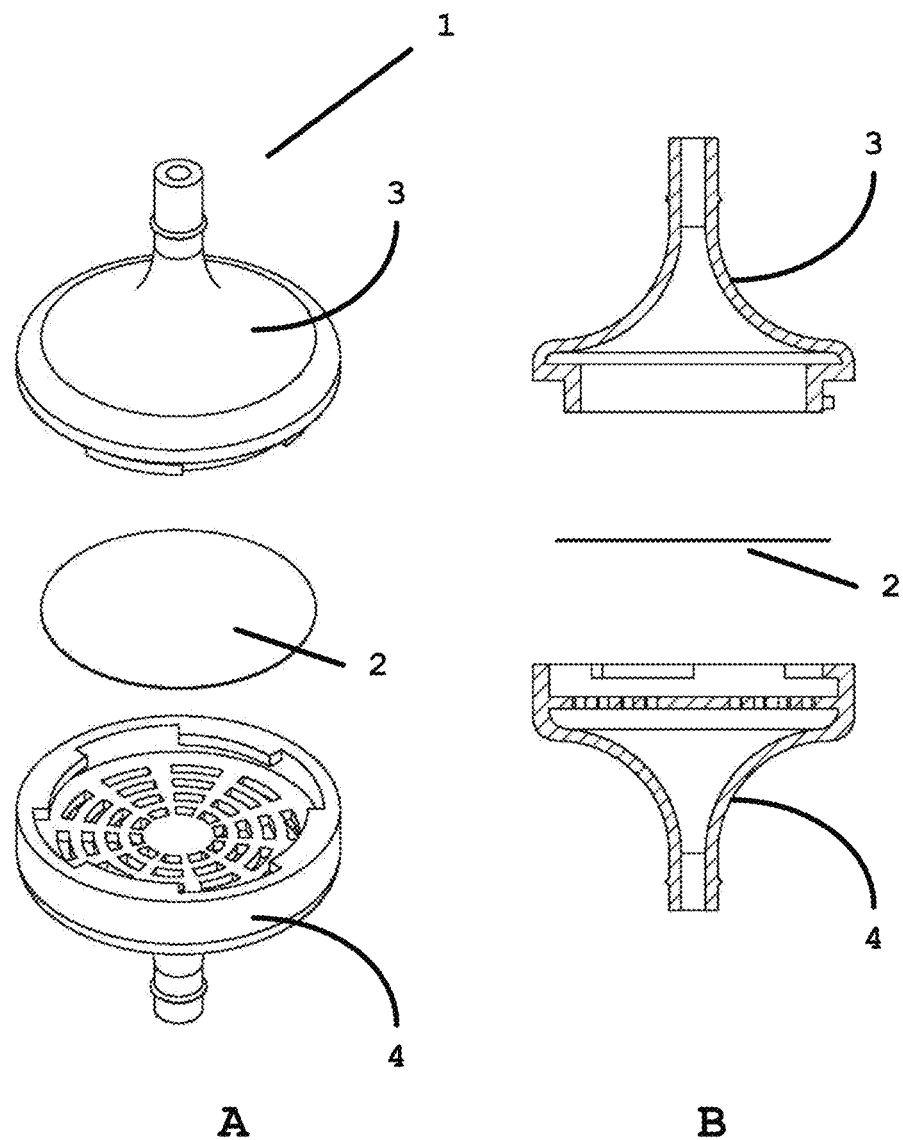
FIG. 16. Perspective (A) and side (B) views of a disassembled filter assembly (1) comprising a functionalised porous membrane (2) prepared according to the method of the first aspect of the invention and sealed between an inlet housing (3) and an outlet housing (4).
Figure 17:
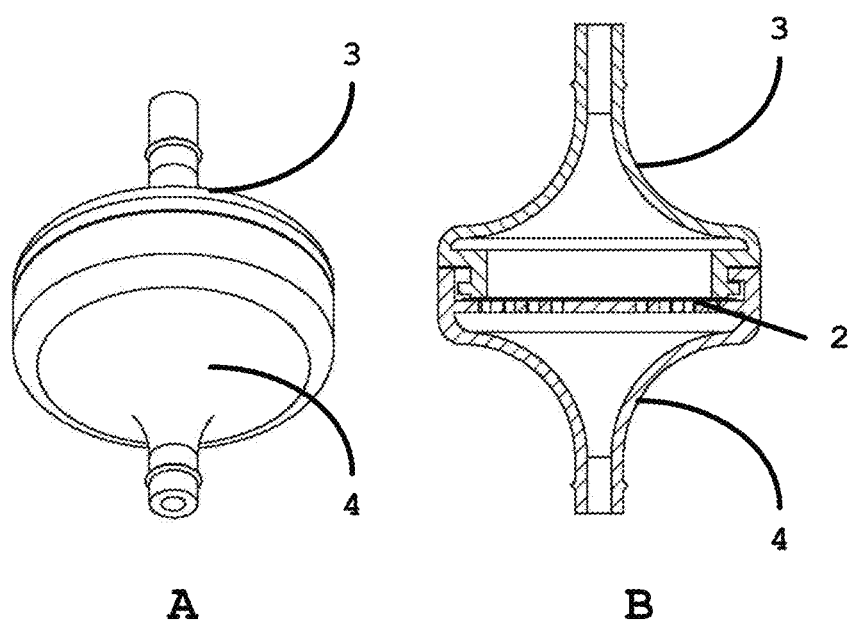
FIG. 17. Perspective (A) and side (B) views of the assembled filter assembly comprising a functionalised porous membrane (2) prepared according to the method of the first aspect of the invention and sealed between an inlet housing (3) and an outlet housing (4).

A 50 µL volume of the suspension of FSL-Biotin modified bacterial cells was mixed with a 50 µL volume of the avidinylated functionalised microspheres. The mixture was incubated at room temperature (circa 22° C.) for 30 minutes before examination by light microscopy. Bacterial cells were observed to be localised to the surface of the avidinylated functionalised microspheres (see FIG. 15 and FIG. 16).

EXAMPLE 8

The polycation lipid construct designated spm-Ad-DOPE (9a) was prepared and isolated as its trifluoroacetic acid (TFA) salt (SCHEME I). Briefly, desymmetritisation of the polyamine spermine [CAS RN 71-44-3] (2) was performed according to a modified version of the method disclosed in the publication of Geall and Blagbrough (2000) employing Boc as the protecting group. It will be recognised that the method is also applicable to the desymmetritisation of other unbranched polyamines such as spermidine [CAS RN 124-20-9] (1), tetraethylenepentamine [CAS RN 112-57-2] (3); pentaethylenehexamine [CAS RN 4067-16-7] (4) and hexaethyleneheptamine [4403-32-1] (5).

Accordingly, a series of polycation lipid constructs may be accessed according to SCHEME I.

According to SCHEME I the Boc protected, desymmetritised intermediate $N^1,N^4,N^9$-tri-tert-butoxycarbonyl)-1,12-diamino-4,9-diazadodecane (6) is conjugated to the diacylglycerophospholipid 1,2-O-dioleoyl-sn-glycero-3-phosphatidyl-ethanolamine [CAS RN 4004-05-1] (DOPE) using the homobifunctional crosslinker disuccinimidyl adipate. It will be recognised that other disuccinimidyl compounds may be employed as the homobifunctional crosslinker. These include The activated lipid (7a) acylates the terminal, primary amino group of $N^1,N^4,N^9$-tri-tert-butoxycarbonyl)-1,12-diamino-4,9-diazadodecane (6) to provide a lipidated Boc protected polyamine intermediate (8a). Again, it will be recognised that according to SCHEME I other diacylglycerophospholipids, such as 1,2-O-distereoyl-sn-glycero-3-phosphatidylethanolamine (DSPE) may be substituted for DOPE.

In the final step of SCHEME I the lipidated polyamine intermediate (8a) is deprotected and the polycation lipid construct (9a) isolated as its trifluoroacetic acid salt.

Materials and Methods

Chloroform, dichloroethane, dichloromethane, methanol and toluene were obtained from Chimmed (Russian Federation). Trifluoroacetic acid, triethylamine, di-tert-butyldicarbonate methyl trifluoroacetate were obtained from Merck (Germany). Spermine was obtained from Sigma-Aldrich (USA). Sephadex LH-20 was obtained from Amersham Biosciences AB (Sweden). Silica gel 60 was obtained from Merck (Germany). Thin layer chromatographic (TLC) analysis was performed on silica gel 60 $F_{254}$ plates (Merck). Amino containing compounds were detected using ninhydrin reagent. DOPE containing compounds were detected using an aqueous solution of potassium permanganate ($KMnO_4$) or by soaking in 8% (w/v) phosphoric acid in water followed by heating at over 200° C. $^1$H NMR spectra were recorded at 30° C. with a Bruker BioSpin GmbH 700 MHz instrument using the signal of the solvent's residual protons as reference ([D]$CHCl_3$, 7.270 ppm; [$D_2$]$H_2O$, 4.750 ppm). Mass spectra were recorded with an Agilent ESI-TOF 6224 LC/MS spectrometer.

Preparation of $Boc_3$Spm (6)

To a stirred solution of spermine (2) (1 equivalent, 1.34 g, 6.6 mmol) in methanol (90 mL) at −80° C. under nitrogen, a solution of methyl trifluoroacetate (1.1 equivalents, 0.730 mL, 7.26 mmol) in methanol (1.5 mL) was added drop-wise over a period of 30 min. Stirring was continued at −80° C. for a further period of 30 min and then the temperature increased to 0° C. The reaction afforded predominantly the mono-trifluoroacetamide. Without isolation, the remaining amino functional groups were quantitatively protected by drop-wise addition of an excess of di-tert-butyldicarbonate (4 equivalents, 5.76 g, 26.4 mmol) in methanol over a period of 3 min. The reaction was then warmed to 25° C. and stirred for a further 15 hr to afford the fully protected spermine ($R_f$ 0.33 (95:5 (v/v) $CHCl_3$-i-PrOH)). The trifluoroacetate protecting group was then removed in situ by increasing the pH of the solution to greater than 11 pH units with concentrated aqueous ammonia (conc. aq. $NH_3$) and then stirred at 25° C. for a period of 15 hr. The solution was concentrated in vacuo and the residue purified over silica gel (95:5:1 to 90:10:1 (v/v/v) $CHCl_3$-MeOH-conc. aq. $NH_3$) to afford the title compound (6) as a colourless homogeneous oil (1.5 g, 45%), $R_f$ 0.32 (83:16:1 (v/v/v) $CHCl_3$-MeOH-conc. aq. $NH_3$). MS, m/z: found 502.3725 (M+1), $C_{25}H_{50}N_4O_6$ required $M^+$ 501.3652.

$^1$H-NMR (700 MHz, $CDCl_3$, 303° K), δ, ppm: 3.4 (m, 2H, 1-$CH_2$), 3.05-3.30 (m, 8H, 3,4,7,8-$CH_2$), 3.01 (m, 2H, 10-$CH_2$), 2.03 (m, 2H, 9-$CH_2$), 1.67 (m, 2H, 2-$CH_2$), 1.50 (m, 4H, 5,6-$CH_2$), 1.44, 1.45, 1.46 (3 s, overlapping, 27H, 3O—C($CH_3$)$_3$).

Preparation of SuO-Ad-DOPE (7a) and SuO-Ad-DSPE (7b)

To a solution of disuccinimidyl adipate (70 mg, 205 μmol) in dry N,N-dimethylformamide (1.5 ml) were added DOPE or DSPE (40 mol) in chloroform (1.5 ml) followed by triethylamine (7 μl). The mixture was kept for 2 h at room temperature, then neutralized with acetic acid and partially concentrated in vacuo. Column chromatography (Sephadex LH-20, 1:1 (v/v) chloroform-methanol, 0.2% (w/v) aqueous acetic acid) of the residue yielded SuO-Ad-DOPE (7a)(37 mg, 95%) as a colourless syrup. TLC (6:3:0.5 (v/v/v) chloroform-methanol-water) $R_f$ 0.5 (SuO-Ad-DOPE (7a)) and $R_f$ 0.55 (SuO-Ad-DOPE (7b)).

$^1$H NMR (2:1 (v/v) $CDCl_3$/$CD_3OD$) δ:

SuO-Ad-DOPE (7a)—5.5 (m, 4H, 2×(—C$\underline{H}$=C$\underline{H}$—), 5.39 (m, 1H, —O$CH_2$—C$\underline{H}$O—$CH_2$O—), 4.58 (dd, 1H, J=3.67, J=11.98, —CCOOHC$\underline{H}$—CHO—$CH_2$O—), 4.34 (dd, 1H, J=6.61, J=11.98, —CCOO $\underline{H}$CH—CHO—$CH_2$O—), 4.26 (m, 2H, PO—C$\underline{H}_2$—$CH_2$—$NH_2$), 4.18 (m, 2H, —C$\underline{H}_2$—OP), 3.62 (m, 2H, PO—$CH_2$—C$\underline{H}_2$—$NH_2$), 3.00 (s, 4H, ONSuc), 2.8 (m, 2H, —C$\underline{H}_2$—CO (Ad), 2.50 (m, 4H, 2×(—C$\underline{H}_2$—CO), 2.42 (m, 2H, —C$\underline{H}_2$—CO (Ad), 2.17 (m, 8H, 2×(—C$\underline{H}_2$—CH=CH—$CH_2$—), 1.93 (m, 4H, COC$H_2$C$\underline{H}_2$C$\underline{H}_2$CO), 1.78 (m, 4H, 2×(COC$H_2$C$\underline{H}_2$—), 1.43, 1.47 (2 bs, 40H, 20 $CH_2$), 1.04 (m, 6H, 2 $CH_3$).

SuO-Ad-DSPE (7b)—5.39 (m, 1H, —O$CH_2$—C$\underline{H}$O—$CH_2O$—), 4.53 (dd, 1H, J=3.42, J=11.98, —CCOO $\underline{H}$CH—CHO—$CH_2$O—), 4.33 (dd, 1H, J=6.87, J=11.98, —CCOO$\underline{H}$CH—CHO—$CH_2$O—), 4.23 (m, 2H, PO—C$\underline{H}_2$—$CH_2$—$NH_2$), 4.15 (m, 2H, —C$\underline{H}_2$—OP), 3.61 (m, 2H, PO—$CH_2$—C$\underline{H}_2$—$NH_2$), 3.00 (s, 4H, ONSuc), 2.81 (m, 2H, —C$\underline{H}_2$—CO (Ad), 2.48 (m, 4H, 2×(—C$\underline{H}_2$—CO), 2.42 (m, 2H, —C$\underline{H}_2$—CO (Ad), 1.93 (m, 4H, COC$H_2$C$\underline{H}_2$C $\underline{H}_2$CO), 1.78 (m, 4H, 2×(COC$H_2$C$\underline{H}_2$—), 1.43, 1.47 (2 bs, 40H, 20 $CH_2$), 1.04 (m, 6H, 2 $CH_3$).

Preparation of $Boc_3$Spm-Ad-DOPE (8a)

To a stirred solution of $Boc_3$Spm (6) (552 mg, 1.1 mmol) in dichloroethane (25 ml) was added trimethylamine (1 ml, 7.2 mmol) followed by a solution of SuO-Ad-DOPE (1066 mg, 1.1 mmol) in dichloroethane (25 ml). The reaction mixture was stirred for a period of 2 hr and then the solvent was removed under reduced pressure at 37° C. The crude product was purified by chromatography on silica gel by elution with 97:3 to 85:15 (v/v) $CHCl_3$-MeOH to afford the title compound (8a) (1.16 g, 78%) as a viscous oil. TLC (10:6:0.8 (v/v/v) $CH_2Cl_2$-EtOH-$H_2O$) $R_f$ 0.36.

$^1$H NMR (700 MHz, $CDCl_3$/$CD_3OD$ 1:1, 10 mg/mL, 303° K) δ, ppm: 5.34 (m, 4H; 2C$\underline{H}$=C$\underline{H}$), 5.19 (m, 1H; O$CH_2$C $\underline{H}$$CH_2$O), 4.37 (dd, $J_{gem}$~11.1 Hz, 1H, POC$H_2$—CH—C $\underline{H}^a$—O(CO)), 4.13 (dd, J~7.2 Hz, 1H, POC$H_2$—CH—C $\underline{H}^b$—O(CO)), 3.94 (m, 4H), 3.48 (m, 2H), 3.05-3.30 (m, 12H, 1,3,4,7,8,10-$CH_2$), 2.71 (m, 2H), 2.20-2.42 (m, 8H), 1.98-2.04 (m, 8H), 1.64 (m, 8H), 1.58 (m, 4H), 1.49 (m, 4H, 5,6-$CH_2$), 1.44, 1.45, 1.46 (3s, 27H, 3O—C($CH_3$)$_3$), 1.22-1.37 (m, 40H, 20 $CH_2$), 0.88 and 0.89 (2d, J≈7 Hz, 6H, 2 $CH_3$).

Preparation of Spm-Ad-DOPE (9a)

To a stirred solution of 8a (1.16 g, 0.85 mmol) in $CHCl_3$ (10 ml) at 25° C. TFA (5 ml, 95%) was added. After a period of 20 min the solution was concentrated in vacuo at 35° C. and the residue was co-evaporated with toluene (5 times 10 mL) to remove trace amounts of TFA. To remove any low molecular weight impurities the residue was dissolved in 1:1 (v/v) $CHCl_3$-MeOH (2 mL) and passed in two portions through a Sephadex LH-20 column (volume 330 mL, eluent 1:1 (v/v) $CHCl_3$-MeOH). Fractions containing pure 9a (di-TFA salt) were combined and evaporated to dryness and the residue dissolved in water (~100 mL) and freeze-dried. A yield of was 975 mg (89%) was obtained. MS, m/z: found 1056.8063 ($M^+$+1), $C_{57}H_{110}N_5O_{10}P$ required $M^+$ 1055.779.

$^1$H NMR (700 MHz, 1:1 (v/v) $CDCl_3$-$CD_3OD$, 10 mg/mL, 303° K) δ, ppm: 5.51 (m, 4H; 2C$\underline{H}$=C$\underline{H}$), 5.42 (m, 1H; O$CH_2$C$\underline{H}$$CH_2$O), 4.6 (dd, $J_{gem}$=12.1 Hz, J=2.81 Hz, 1H, POC$H_2$—CH—C$\underline{H}^a$—O(CO)), 4.34 (dd, J=7.09 Hz, 1H, POC$H_2$—CH—C$\underline{H}^b$—O(CO)), 4.14 (m, 2H, POC $\underline{H}_2$$CH_2$N), 4.06 (m, 2H, POC$H_2$—CH—$CH_2$), 3.59 (m, 2H, O$CH_2$C$\underline{H}_2$N), 3.49 (m, 2H, 1-$CH_2$), 3.11-3.28 (m, 10H, 3,4,7,8,10-$CH_2$), 2.42 and 2.51 (2m, 8H, 4 COC$\underline{H}_2$), 2.26 (m, 2H, 2-$CH_2$), 2.19 (m, 8H, 2C$\underline{H}_2$CH=CHC$\underline{H}_2$), 2.07 (m, 2H, 9-$CH_2$), 1.99 (m, 4H, 5,6-$CH_2$), 1.79 (m, 8H, 4 COC $H_2$C$\underline{H}_2$), 1.40-1.54 (m, 40H, 20 $CH_2$), 1.05 and 1.06 (2t, J 7 Hz, 6H, 2 $CH_3$).

Surface Treatment—Micro-Dimensioned Particle (Biotic Origin) Adherence

A stock solution of the construct designated Spm-Ad-DOPE (9a) was prepared in methanol at a concentration of 10 mg/mL. The stock solution was diluted to a concentration of 250 μg/mL in methanol and 25 μL volumes of the diluted stock solutions dispensed into each of the round bottomed wells of a multi-well microplate (Corning Inc.). The plates were allowed to dry before washing the wells 6 times with deionized water. Control wells were similarly treated using either methanol alone (blank) or substituting the construct designated Biotin-CMG(2)-Ad-DOPE as described in the specification accompanying international application no. PCT/NZ2008/000266 [publ. no. WO 2009/048343]).

Red blood cells (RBCs; group O, up to 2 weeks old) were washed and resuspended at a concentration of 1% packed cell volume (pcv) in phosphate-buffered saline (PBS). A 50 µL volume of the suspension of RBCs was dispensed into each of the wells and incubated for 1 hour at room temperature before washing 6 times with PBS. The RBCs were fixed by adding a 50 µL volume of a solution of glutaraldehyde in PBS at a concentration of 2.5% (w/v) and incubating for 10 minutes before washing each well with water and allowing to dry. The RBCs were lysed by adding a 50 µL volume of deionized water and incubating for 10 minutes before discarding the water and allowing to dry.

Figure 18:
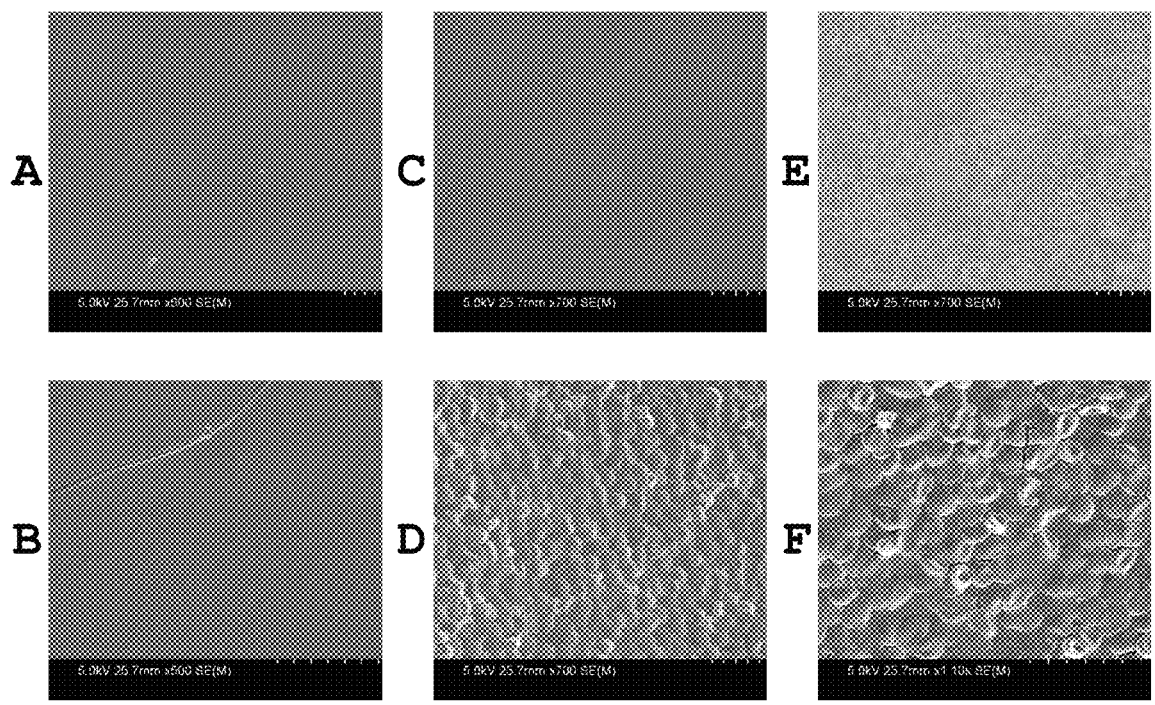
FIG. 18. Scanning electron micrographs at the magnifications indicated in each micrograph of the surface of Capture-R™ Ready-Id (A), Capture-R™ Ready-Screen (B), CT-6 (C), Spm-Ad-DOPE (9a) treated and fixed (D), Spm-Ad-DOPE (9a) treated and lysed (E) and untreated (F) plates.

For scanning electron microscopy (SEM) the bottom of each well was cut from the plate and the treated surface sputter coated with platinum prior to imaging. The images obtained at increasing magnification for well surfaces treated according to the methods described and those obtained for commercially available plates (Capture-R™ Ready-Id, Capture-R™ Ready-Screen and CT-6; Immucor Inc.) are provided in FIG. 18.

Adherence of RBCs to well surfaces treated according to the method described was clearly evident. Investigations were performed to determine if the adherence could be attributable to the use of the construct designated Spm-Ad-DOPE (9a) or the polycation spermine (2) alone. A stock solution of spermine (2) was prepared at a concentration of 10 mg/mL in methanol. The spermine stock solution was diluted to a concentration of 0.2 mg/mL in either methanol or water. Volumes of 200 µL of diluted stock solution (approximately 950 µM) of the construct designated Spm-Ad-DOPE (9a), spermine (2) in methanol or spermine in water were added to each of the first wells of a microplate. A two-fold serial dilution from each of the first wells was then performed. The microplate was then dried under vacuum before washing each well of the microplate with deionized water by immersing and discarding the wash water 4 times. After drying, 50 µL volumes of a suspension of RBCs at a concentration of 1% pcv in either 10 mM Tris/0.25 M sucrose (SucT) or PBS were dispensed into each well. (Aggregation of RBCs was observed in wells where the construct designated Spm-Ad-DOPE (9a) had been added at a concentration of 29 µM or greater.) The plate was incubated for one hour at room temperature before washing the wells 6 times with PBS.

SCHEME I

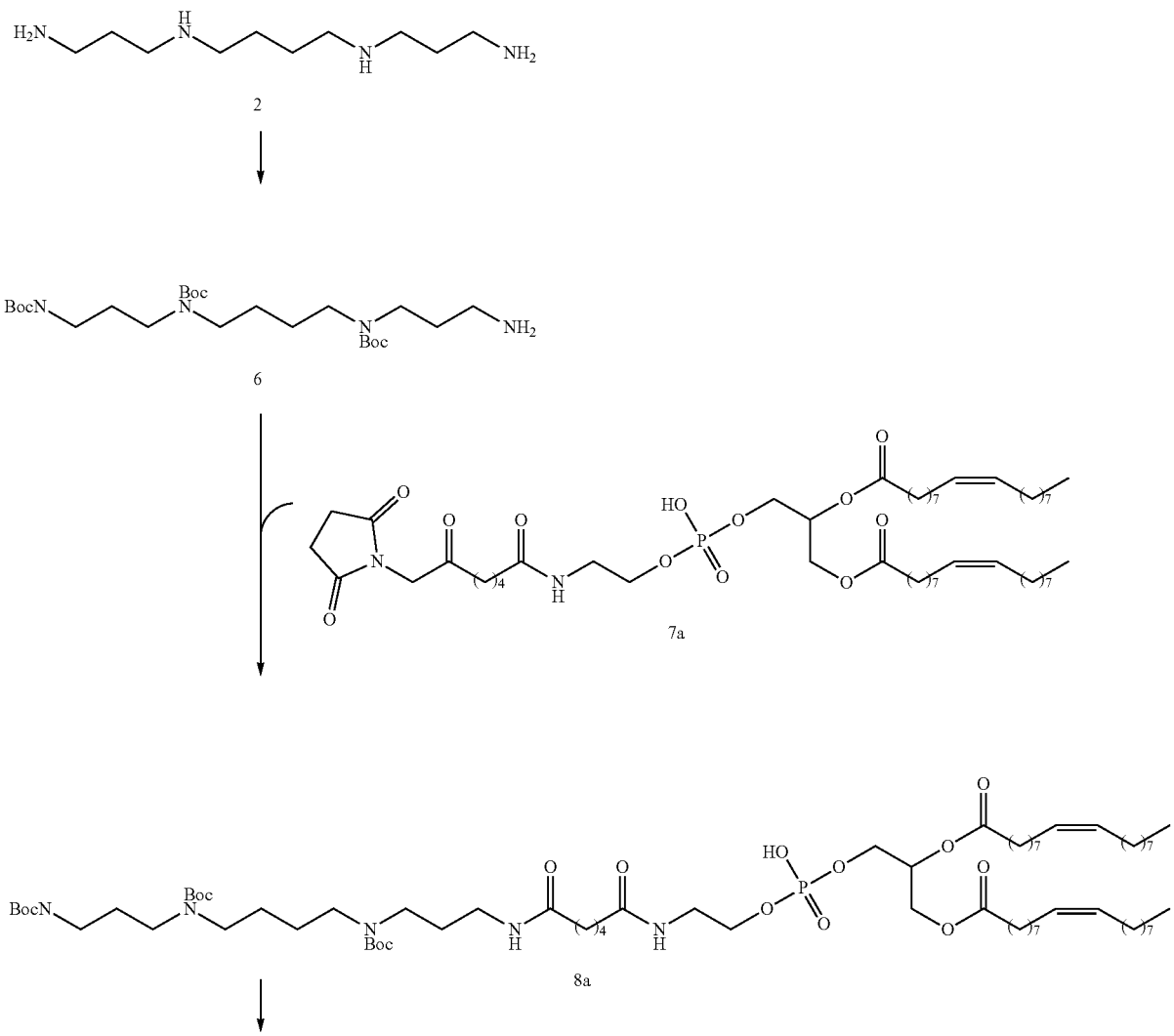

-continued

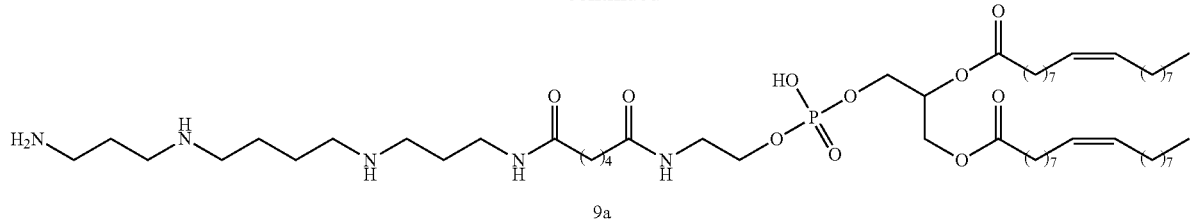

9a

Figure 19:
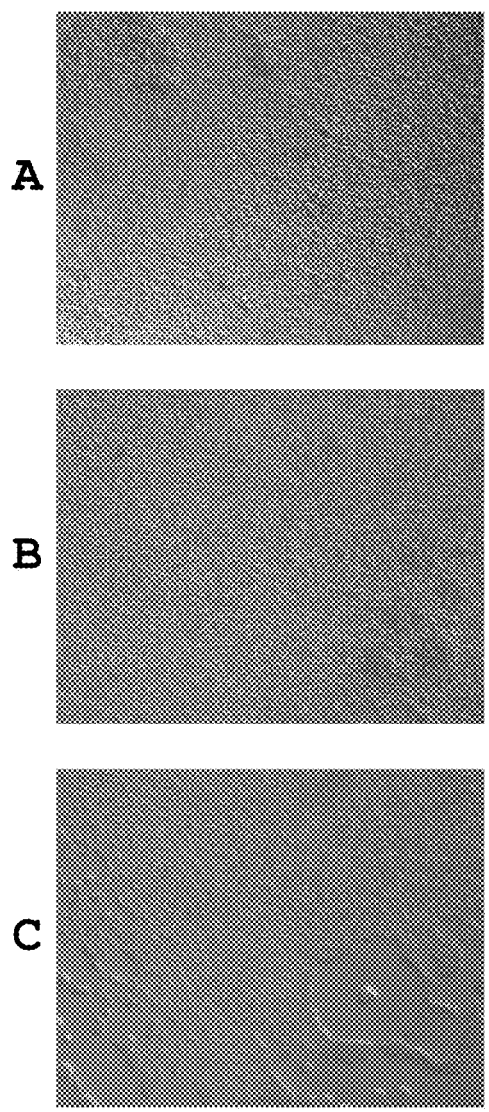
FIG. 19. Photomicrographs (100×) of surfaces treated with Spm-Ad-DOPE (9a) in either PBS (A) or SucT (B) or spermine (C) following contact with a suspension of RBCs.

Following drying the plate was inverted and the base of the wells examined by light microscopy (100× magnification) for the presence of a uniform monolayer of RBCs. Photomicrographs obtained for wells treated with a solution of either the construct designated Spm-Ad-DOPE (9a) or spermine (2) alone are presented in FIG. 19. A uniform monolayer of cells was observed in wells treated with the construct designated Spm-Ad-DOPE (9a) at concentrations of 14 to 237 μM (0.015 to 0.25 mg/mL) in either of the two buffers (SucT or PBS) used. Any attachment of cells when spermine (2) alone was used was not uniform or reproducible. No cells were observed to adhere to the surface in wells containing spermine (2) alone in water.

Surface Treatment—Micro-Dimensioned Particle (Abiotic Origin) Adherence

Figure 20:
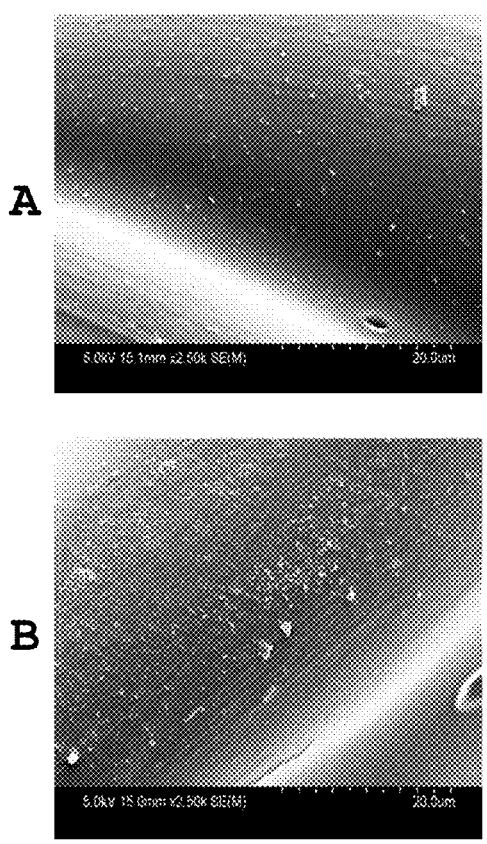
FIG. 20. Scanning electron micrographs of the surface of untreated (A) and treated (B) laminated nylon mesh following exposure to particulates generated by a wood burner.

A volume of 100 μL of a solution of 0.05% (w/v) bromophenol blue and 50 μM of the construct designated KODE-spm in water was dispensed and spread across the surface of a strip of laminated nylon mesh. The strip was allowed to dry for one hour at room temperature before being exposed to particulates released from either smoking cigarettes or a wood burner using an artificial syringe as a "puffer" (exposure for about 10 minutes). The exposed strips were stored in a sealed polythene bag before being examined by scanning electron microscopy (SEM) (FIG. 20).

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention.

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention.

REFERENCED PUBLICATIONS

Geall and Blagbrough (2000) *Homologation of polyamines in the rapid synthesis of lipospermine conjugates and related lipoplexes* Tetrahedron 56, 2249-2460

Kato et al (2003) *Immobilized culture of nonadherent cells on an oleyl poly(ethylene glycol) ether-modified surface* BioTechniques 35, 1014-1021

The invention claimed is:

1. A method of treating an inert surface of a substrate to improve the adherence to the treated surface of micro-dimensioned particles comprising the steps of:
    contacting the inert surface with in an aqueous dispersion of a construct of the structure F-S-L; and then
    washing the surface with an aqueous vehicle to provide the treated surface, where the substrate is the fibres of a filter; F is a polyamine; S is —CO(CH$_2$)$_2$CO—, —CO(CH$_2$)$_3$CO—, —CO(CH$_2$)$_4$CO— or —CO(CH$_2$)$_5$CO—; and L is a diacyl- or dialkyl-glycerophospholipid.

2. The method of claim 1 where the filter is an air filter.

3. The method of claim 2 where the inert surface consists of a polymer.

4. The method of claim 3 where F is of the structure:

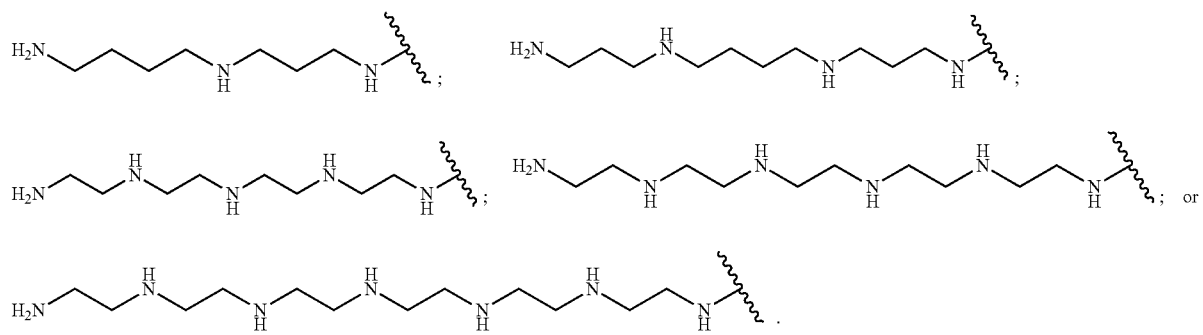

5. The method of claim 4 where the polymer is selected from the group consisting of: polyamide, polycarbonate, polypropylene, polyethersulfone, polytetrafluoroethylene and polyvinylidene fluoride.
6. The method of claim 5 where L is a phosphatidylethanolamine.
7. The method of claim 6 where the construct is of the structure:
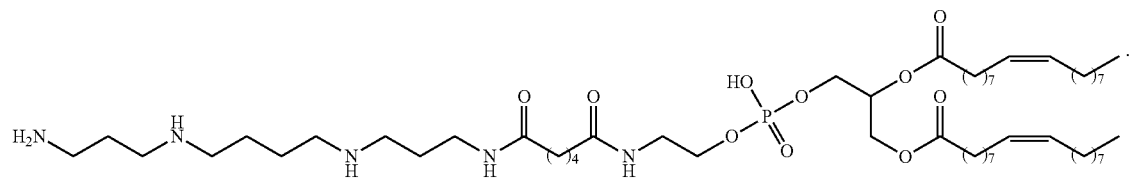
* * * * *